(12) United States Patent
Bar-El et al.

(10) Patent No.: US 11,207,465 B2
(45) Date of Patent: Dec. 28, 2021

(54) CARTRIDGE INSERTION FOR DRUG DELIVERY DEVICE

(71) Applicant: West Pharma. Services IL, Ltd., Ra'anana (IL)

(72) Inventors: Yossi Bar-El, Beit Arye (IL); gil Yigal, Gan Yavne (IL); Reuven Y. Filman, Netanya (IL)

(73) Assignee: West Pharma. Services IL. Ltd., Ra'anana (IL)

( * ) Notice: Subject to any disclaimer, the term of this patent is extended or adjusted under 35 U.S.C. 154(b) by 59 days.

(21) Appl. No.: 15/575,229

(22) PCT Filed: Jun. 3, 2016

(86) PCT No.: PCT/US2016/035720
§ 371 (c)(1),
(2) Date: Nov. 17, 2017

(87) PCT Pub. No.: WO2016/196934
PCT Pub. Date: Dec. 8, 2016

(65) Prior Publication Data
US 2018/0154081 A1    Jun. 7, 2018

Related U.S. Application Data

(60) Provisional application No. 62/171,002, filed on Jun. 4, 2015.

(51) Int. Cl.
*A61M 5/24* (2006.01)
*A61M 5/20* (2006.01)
*A61M 5/142* (2006.01)

(52) U.S. Cl.
CPC ...... *A61M 5/2422* (2013.01); *A61M 5/14244* (2013.01); *A61M 5/2033* (2013.01);
(Continued)

(58) Field of Classification Search
CPC ............ A61M 5/2422; A61M 5/14244; A61M 5/2033; A61M 5/2053; A61M 5/24;
(Continued)

(56) References Cited

U.S. PATENT DOCUMENTS 5,505,709 A    4/1996  Funderburk et al.
5,741,227 A    4/1998  Sealfon
(Continued)

FOREIGN PATENT DOCUMENTS

CN     102378638 A2    3/2012
EP       2364741 A1    9/2011
(Continued)

OTHER PUBLICATIONS

Int'l Preliminary Report on Patentability dated Dec. 5, 2017 in In'tl Application No. PCT/US2016/035720.
(Continued)

*Primary Examiner* — Brandy S Lee
*Assistant Examiner* — Nidah M Hussain
(74) *Attorney, Agent, or Firm* — BakerHostetler

(57) ABSTRACT

A method and assembly are disclosed for interfacing between a drug cartridge and a drug delivery device. Optionally, the drug delivery device includes a compartment that retains the cartridge during drug delivery and/or a stopper pushing assembly mounted to the device behind (proximal to) the compartment. In some embodiments, the cartridge may be inserted laterally into the compartment in front of the pushing assembly. For example, the delivery device may include a moving cartridge bay. The cartridge is optionally inserted into the bay and/or the bay and cartridge optionally move into the cartridge compartment. Alternatively or additionally, the cartridge compartment may have a proximal opening into which the cartridge is inserted and/or the pushing assembly may be moved into position after insertion
(Continued)

of the cartridge. In some embodiments the cartridge may have a distal seal that is broken by a longitudinal movement.

15 Claims, 24 Drawing Sheets

(52) U.S. Cl.
CPC ............ *A61M 5/2053* (2013.01); *A61M 5/24* (2013.01); *A61M 5/2466* (2013.01); *A61M 2005/2414* (2013.01); *A61M 2005/2437* (2013.01); *A61M 2005/2477* (2013.01); *A61M 2005/2496* (2013.01)

(58) Field of Classification Search
CPC ........ A61M 5/2466; A61M 2005/2496; A61M 2005/2407
USPC ....................................................... 604/500
See application file for complete search history.

(56) References Cited

U.S. PATENT DOCUMENTS

| | | | |
|---|---|---|---|
| 5,925,018 | A | 7/1999 | Ungerstedt |
| 5,954,697 | A | 9/1999 | Srisathapat et al. |
| 6,736,796 | B2 | 5/2004 | Shekalim |
| 6,800,071 | B1 | 10/2004 | McConnell et al. |
| 7,214,209 | B2 | 5/2007 | Mazzoni |
| 7,377,907 | B2 | 5/2008 | Shekalim |
| 8,157,769 | B2 | 4/2012 | Cabiri |
| 8,465,455 | B2 | 6/2013 | Cabiri |
| 8,679,062 | B2 | 3/2014 | Yodfat et al. |
| 8,945,051 | B2 | 2/2015 | Schriver et al. |
| 9,421,321 | B2 | 8/2016 | Hanson et al. |
| 9,492,618 | B2 | 11/2016 | Day |
| 9,572,926 | B2 | 2/2017 | Cabiri |
| 10,765,808 | B2 | 9/2020 | Day et al. |
| 2006/0253086 | A1* | 11/2006 | Moberg ............ A61M 5/14248 604/272 |
| 2009/0093792 | A1* | 4/2009 | Gross .................. A61M 5/1456 604/518 |
| 2012/0035546 | A1 | 2/2012 | Cabiri |
| 2012/0116311 | A1 | 5/2012 | Bruggemann et al. |
| 2012/0172804 | A1 | 7/2012 | Plumptre |
| 2013/0110049 | A1 | 5/2013 | Cronenberg et al. |
| 2013/0245596 | A1 | 9/2013 | Cabiri et al. |
| 2013/0245604 | A1 | 9/2013 | Kouyoumjian et al. |
| 2013/0253472 | A1 | 9/2013 | Cabiri |
| 2013/0296799 | A1 | 11/2013 | Degtiar et al. |
| 2013/0304021 | A1 | 11/2013 | Cabiri et al. |
| 2015/0165121 | A1 | 6/2015 | Murakami et al. |
| 2015/0224258 | A1 | 8/2015 | Holtwick et al. |
| 2016/0038691 | A1 | 2/2016 | Mounce et al. |
| 2016/0051765 | A1 | 2/2016 | Morris et al. |
| 2016/0051767 | A1 | 2/2016 | Higgins et al. |
| 2016/0136353 | A1 | 5/2016 | Adams |
| 2016/0158436 | A1 | 6/2016 | Yang |
| 2016/0199592 | A1 | 7/2016 | Eggert et al. |
| 2016/0317736 | A1 | 11/2016 | Schabbach et al. |
| 2016/0317737 | A1 | 11/2016 | Schabbach et al. |
| 2017/0106138 | A1 | 4/2017 | Cabiri |

FOREIGN PATENT DOCUMENTS

| | | |
|---|---|---|
| EP | 2862588 A1 | 4/2015 |
| JP | 2013521084 A | 6/2013 |
| WO | 2011090956 A2 | 7/2011 |
| WO | 2012032411 A2 | 3/2012 |
| WO | WO 2012/032411 A2 * | 3/2012 |

OTHER PUBLICATIONS

Int'l Search Report and Written Opinion dated Aug. 12, 16 in Int'l Application No. PCT/US2016/035720.
Office Action dated Nov. 29, 2019 in CN Application No. CN 201680032632.3.

* cited by examiner

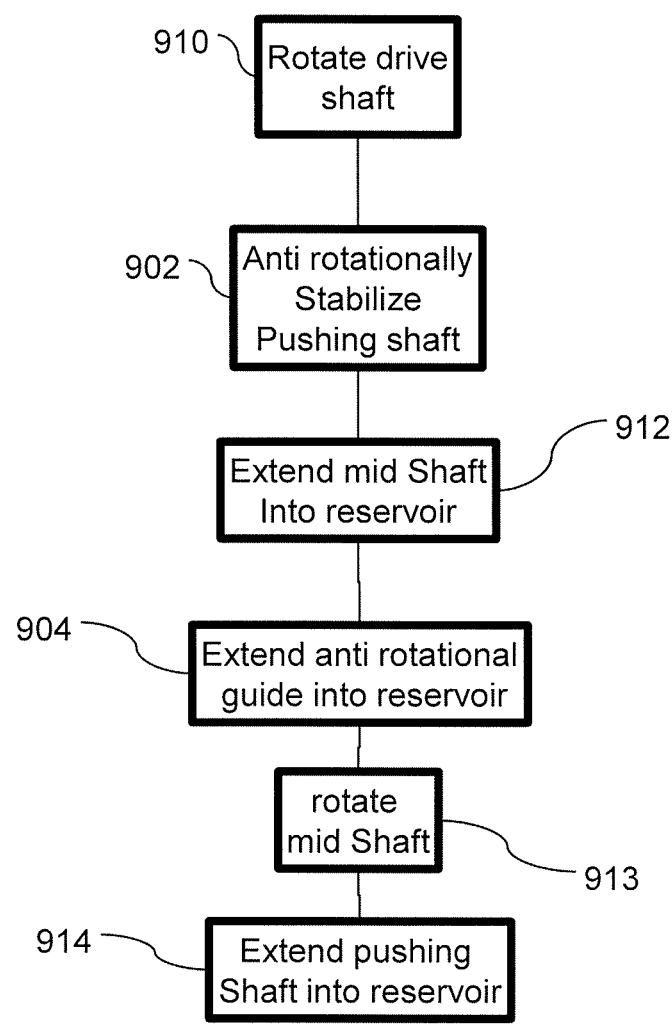

CARTRIDGE INSERTION FOR DRUG DELIVERY DEVICE

CROSS-REFERENCE TO RELATED APPLICATION

This application is a section 371 of International Application No. PCT/US2016/035720, filed Jun. 3, 2016, which was published in the English language on Dec. 8, 2016 under International Publication No. WO 2016/196934 A1, which claims the benefit of priority under 35 USC 119(e) of U.S. Provisional Patent Application No. 62/171,002 filed Jun. 4, 2015, the contents of which are incorporated herein by reference in their entirety.

FIELD AND BACKGROUND OF THE INVENTION

The present invention, in some embodiments thereof, relates to a cartridge insertion assembly for a drug delivery device and, more particularly, but not exclusively, to an insertion assembly for a drug device including an internal telescoping assembly.

U.S. Pat. No. 6,800,071 discloses, "an improved pump, reservoir and reservoir piston for," "controlled delivery of fluids. A motor is operably coupled to a drive member, such as a drive screw, which is adapted to advance a plunger slide in response to operation of the motor. The plunger slide is removably coupled to the piston. The piston comprises a first member and a second member. The first member has an external proximate side and an external distal side. The external proximate side is adapted to contact the fluid and is made of a material having a first stiffness. The second member has a first side and a second side and is at least partially disposed within the first member. The first side of the second member is adjacent to the external proximate side of the first member and is made of a material having a stiffness which is greater than the first stiffness."

U.S. Patent Application Publication No. 2013/0253472 to Cabiri discloses, "A method and apparatus," . . . "for delivery of a drug to a recipient. In some embodiments, the delivery apparatus may unseal a drug containing reservoir. In some embodiments, the delivery rate may be controlled and/or adjustable. Optionally the apparatus may be disposable. Optionally, the apparatus may have a low profile and/or be wearable and/or attachable to the recipient. Optionally, discharge of the drug and/or unsealing of the reservoir may be driven by a plunger moving parallel to the base of the apparatus. Optionally, the apparatus may release a hypodermic needle into the recipient. Optionally, release of the hypodermic needle may be in a direction non-parallel and/or orthogonal to the direction of movement of the plunger.

Optionally, prior to release, the hypodermic needle may be preserved in an aseptic state by a needle opening septum sealing a needle opening. Optionally, upon release, the hypodermic needle may pierce the needle opening septum."

Additional background art includes International Patent Application Publication No. WO/2011/090956 by Cabiri, U.S. Patent Application Publication No. 2009/0093792 to Gross, U.S. Patent Application Publication 20130304021, U.S. Patent Application Publication 20130296799, U.S. Patent Application Publication 20130245596, U.S. Pat. No. 8,465,455, International Patent Application Publication No. WO/2011/090956 and U.S. Patent Application Publication No. 2009/0093792.

Examples of syringe stoppers actuated by telescopic assemblies can be found for example in International Patent Application Publication No. WO/2011/090956 to Cabiri and/or U.S. Patent Application Publication No. 2009/0093792 to Gross which are herein incorporated in their entirety by reference.

SUMMARY OF THE INVENTION

Unless otherwise defined, all technical and/or scientific terms used herein have the same meaning as commonly understood by one of ordinary skill in the art to which the invention pertains. Although methods and materials similar or equivalent to those described herein can be used in the practice or testing of embodiments of the invention, exemplary methods and/or materials are described below. In case of conflict, the patent specification, including definitions, will control. In addition, the materials, methods, and examples are illustrative only and are not intended to be necessarily limiting.

According to an aspect of some embodiments of the invention, there is provided an interface for connecting a cylindrical reservoir to a drug delivery device having a skin contact surface comprising: a coupler attached to the drug delivery device independent of the cylindrical reservoir; the coupler sized and shaped to form a flow path between a distal opening of the cylindrical reservoir and a fluid path of the drug delivery device; an expanding assembly attached to the drug delivery device independent of the cylindrical reservoir and expanding along an axis parallel to the skin contact surface; a compartment shaped and sized to hold the cylindrical reservoir with a longitudinal axis of the cylindrical reservoir coaxial to the axis of expansion and a proximal opening of the cylindrical reservoir facing the expanding assembly and a distal opening of the reservoir facing the coupler.

According to some embodiments of the invention, the coupler includes a cannula sized and shaped for piercing a seal of the distal opening of the reservoir.

According to some embodiments of the invention, the interface further comprises: a channel shaped for directing a movement of the reservoir longitudinally along the channel towards the coupler such that the coupler pierces the seal of the distal opening of the reservoir.

According to some embodiments of the invention, the channel is inside the compartment the interface further comprising: a proximal opening of the channel sized and shaped for axial insertion of a proximal end of the reservoir into the channel toward the coupler; and a movable mount connecting the expanding assembly to the delivery device for moving between a first position proximal to the proximal opening of the channel and blocking insertion of the reservoir into the proximal opening of the channel and a second position wherein the expanding assembly is clear of the proximal opening of the channel.

According to some embodiments of the invention, the interface further comprises: a bay including the channel and movably mounted to the delivery device to move between a loading position and a delivery position; wherein in the loading position an opening of the channel is outside of the compartment and in the delivery position the channel and the opening of the channel are in the compartment.

According to some embodiments of the invention, the interface further comprises: a pivot movably attaching the bay to the delivery device.

According to some embodiments of the invention, the opening of the channel is on a proximal portion of the bay and the pivot is on a distal portion of the bay such that when the bay moves from the loading position to the delivery position the opening pivots around the pivot towards the compartment.

According to some embodiments of the invention, the bay moves independently from the coupler such that the coupler is aligned with the channel when the bay is in the delivery position and the coupler is not aligned with the channel when the bay is in the loading position.

According to some embodiments of the invention, the coupler is attached to the bay such that the coupler is aligned with the channel when the bay is in the delivery position and in the loading position.

According to some embodiments of the invention, the coupler is attached to the bay such that when the reservoir is inserted into the bay the coupler forms the flow path while the bay is in the loading position.

According to some embodiments of the invention, the expanding assembly includes a telescoping screw.

According to some embodiments of the invention, the interface further comprises: an opening in the device for inserting the reservoir laterally into the compartment.

According to some embodiments of the invention, the interface further comprises: a hollow needle in fluid communication with the flow path and extending outward from the skin contact surface.

According to an aspect of some embodiments of the invention, there is provided a method of loading a cylindrical reservoir containing a drug into a patch injector having a skin contact surface comprising: providing an expanding assembly mounted to the patch injector independently of the cylindrical reservoir with an axis of expansion parallel to the skin contact surface and also providing a coupler mounted to the patch injector independently from the cylindrical reservoir; positioning the cylindrical reservoir in a compartment of the patch injector between the coupler and an the expanding assembly coaxial to the axis of expansion and with a proximal opening of the cylindrical reservoir facing the expanding assembly and with a distal opening of the cylindrical reservoir facing the coupler; opening a fluid path between the reservoir and an injection device of the patch injector through the distal opening of the reservoir; and expanding the expanding assembly through a proximal opening of the reservoir to push a plunger seal along a longitudinal axis of the reservoir to drive the drug from the reservoir through the distal opening of the reservoir to the fluid path.

According to some embodiments of the invention, the method further comprises: breaking a seal of the distal opening of the cylindrical reservoir with the coupler.

According to some embodiments of the invention, the positioning includes inserting at least a distal portion of the reservoir into the compartment of the patch injector axially towards the coupler through an opening in the compartment and pushing the seal against the coupling after the inserting; and the method further comprising moving the expanding assembly between a first position proximal to the proximal opening and blocking insertion of the reservoir into the proximal opening and a second position wherein the pushing assembly clears the proximal opening.

According to some embodiments of the invention, the method further comprises: Inserting at least a distal portion of the cartridge axially into a channel of a cartridge bay, the inserting and the opening a fluid path occurring while the cartridge bay is in loading position and the proximal opening of the cylindrical reservoir remain outside the compartment; moving the cartridge bay and the cartridge together subsequent to the opening to a delivery position wherein the cartridge is inside the compartment between the expanding assembly and the coupler.

According to some embodiments of the invention, the method further comprises: Inserting at least a distal portion of the cartridge axially into a channel of a cartridge bay in a loading position wherein the proximal opening of the cylindrical reservoir remains outside the compartment; moving the cartridge bay and the cartridge together to position the cartridge inside the compartment between the expanding assembly and the coupler; and wherein the subsequent to the moving, the expanding of the expanding assembly pushes the distal seal of the cartridge against the coupler to cause the opening.

According to some embodiments of the invention, the method further comprises: placing the skin contact surface against a skin of a user; inserting a hollow needle in fluid communication with the fluid path into the user at an angle between 30 to 150 degrees with respect to the axis of expansion.

According to an aspect of some embodiments of the invention, there is provided an interface assembly for drug delivery device a drug cartridge having a seal on a distal portion thereof and a stopper inserted in a proximal opening thereof, the assembly comprising: a cartridge retention compartment; a stopper pushing assembly fixedly mounted to the delivery device proximal to the compartment; a cartridge bay movable mounted to the delivery device; the bay including: a channel fitting at least the distal portion of the cartridge for retaining the cartridge, the channel including a proximal opening sized for insertion of the distal portion of the cartridge longitudinally into the channel and a distal cannula protruding axially into a distal end of the channel for piercing the seal when the distal portion is inserted into the channel, and wherein the bay moves between a loading position wherein the cartridge is inserted into the channel and a delivery position wherein the cartridge is retained inside of the compartment.

Wherein the bay moves between a loading position wherein the cartridge is inserted into said channel and a delivery position wherein said cartridge is retained inside of said compartment.

According to an aspect of some embodiments of the invention, there is provided an interface assembly for drug delivery device a drug cartridge having a seal on a distal end thereof and a stopper inserted in a proximal opening thereof, the assembly comprising: a cartridge retention chamber; a stopper pushing assembly fixedly mounted to the delivery device proximal to the chamber a cartridge bay movable mounted to the delivery device; the bay including: a channel fitting at least a distal portion of the cartridge for retaining the cartridge, the channel including a proximal opening sized for insertion of the distal portion of the cartridge longitudinally into the channel and a distal cannula protruding axially into a distal end of the channel for piercing the seal when the proximal portion is inserted into the channel, and wherein the bay moves between a loading position wherein the cartridge is inserted into the channel and a delivery position wherein the cartridge is retaining inside of the chamber.

According to an aspect of some embodiments of the invention, there is provided an interface assembly for drug delivery device a drug cartridge having a seal on a distal end thereof and a stopper inserted in a proximal opening thereof, the assembly comprising: a cartridge retention chamber; a chamber fitting the cartridge including a proximal opening for insertion of the cartridge a coupler at a distal end of the chamber, the coupler configured to connect the cartridge to a fluid pathway of the delivery device a stopper pushing movable mounted to the delivery device for moving between a first position proximal to the proximal opening and blocking insertion of the cartridge into the proximal opening and a second position wherein the proximal opening is clear for insertion of the cartridge.

According to an aspect of some embodiments of the invention, there is provided a method for interfacing a drug cartridge and a drug delivery device comprising: providing the drug cartridge having a seal on a distal end thereof and a stopper inserted in a proximal opening thereof and also providing a stopper pushing assembly configured for mounting to the delivery device; inserting at least a distal portion of the cartridge into a chamber of the drug device through a proximal opening of the chamber; opening a fluid path between the drug delivery device and the cartridge by pushing the a seal located on a distal end of the cartridge against a coupling mounted to a distal end of the chamber; positioning a cartridge pushing assembly behind the proximal opening.

According to an aspect of some embodiments of the invention, there is provided a method for interfacing a drug cartridge and a drug delivery device comprising: providing the drug cartridge having a seal on a distal end thereof and a stopper inserted in a proximal opening thereof and also providing a stopper pushing assembly configured for mounting to the delivery device; inserting at least a distal portion of the cartridge longitudinally into a channel of movable cartridge bay of the; opening a fluid path between the drug delivery device and the cartridge by pushing the a seal located on a distal end of the cartridge against a coupling mounted to a distal end of the channel; moving the cartridge bay to position the cartridge distal to the cartridge pushing assembly.

According to an aspect of some embodiments of the invention, there is provided a method for interfacing between a drug cartridge and a drug delivery device comprising: coupling a distal opening of the drug cartridge to a flow path of the device; inserting a drug cartridge into the device distal to a stopper pushing assembly mounted to the device; discharging the drug by pushing a stopper distally in the cartridge with the stopper pushing device.

According to an aspect of some embodiments of the invention, there is provided an assembly for interfacing a drug cartridge and a drug delivery comprising: a chamber in the device for holding the cartridge; a coupler for connecting a distal opening of the cartridge to a fluid pathway in the device; an opening in the side of device for inserting the cartridge into the chamber; a stopper pushing assembly mounted to the device proximal to the chamber.

According to an aspect of some embodiments of the invention, there is provided an assembly for interfacing a drug cartridge and a drug delivery comprising: a chamber in the device for holding the cartridge; a coupler for connecting a distal opening of the cartridge to a fluid pathway in the device; a proximal opening in the proximal end of the chamber for inserting the cartridge into the chamber; a stopper pushing assembly movable mounted to the device for moving between a position clearing the proximal opening proximal to the chamber and a position proximal to and blocking the proximal opening of the chamber.

A stopper pushing assembly movable mounted to the device for moving between a position clearing said proximal opening proximal to the chamber and a position proximal to and blocking the proximal opening of the chamber.

BRIEF DESCRIPTION OF THE SEVERAL VIEWS OF THE DRAWINGS

Some embodiments of the invention are herein described, by way of example only, with reference to the accompanying drawings. With specific reference now to the drawings in detail, it is stressed that the particulars shown are by way of example and for purposes of illustrative discussion of embodiments of the invention. In this regard, the description taken with the drawings makes apparent to those skilled in the art how embodiments of the invention may be practiced.

In the drawings:

FIG. 9 is a flow chart illustrating a method of driving a stopper in accordance with an embodiment of the present invention.

DESCRIPTION OF SPECIFIC EMBODIMENTS OF THE INVENTION

Figure 1A:
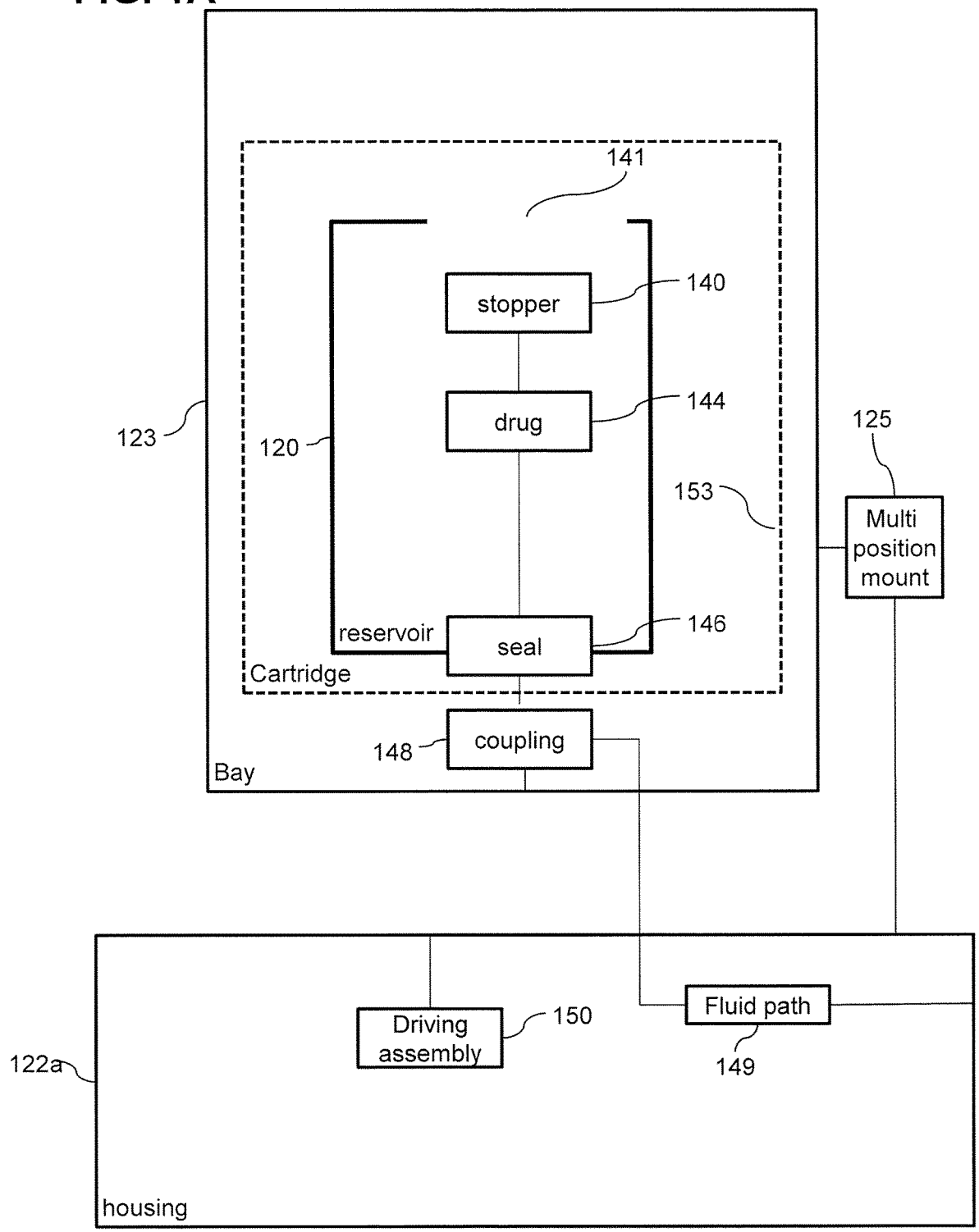
FIG. 1A is a block diagram of a cartridge insertion assembly with a moving cartridge bay in a loading position in accordance with an embodiment of the present invention.

The present invention, in some embodiments thereof, relates to a cartridge insertion assembly for a drug delivery device and, more particularly, but not exclusively, to an insertion assembly for a drug device including an internal telescoping assembly.

Overview

An aspect of some embodiments of the present invention relates to an assembly and method for interfacing between a drug reservoir and a drug delivery device. In some embodiments the interface includes a compartment that retains the cartridge and/or an expanding assembly mounted to the device on one side of the compartment and/or a coupler to a fluid path on an opposing side. Optionally an axis of expansion of the pushing assembly is into the compartment and generally parallel to a skin contact surface of the device. Optionally the reservoir is retained in the compartment coaxial to the axis of expansion of the pushing assembly. For example a distal opening of the reservoir faces and/or is located proximal to and/or is connected to the coupler. Optionally the coupler couples the distal opening to a fluid path of the delivery device. Optionally, when the cartridge is in place the pushing assembly expands into a proximal opening of the reservoir and/or pushes a stopper, for example a plunger seal, distally in the reservoir.

Pushing the plunger seal optionally discharges the drug from the reservoir. For example the drug is discharged out the distal opening to the fluid path.

In some embodiments a cartridge may contain a drug in a cylindrical reservoir.

Optionally the reservoir includes a distal opening and/or a proximal opening.

For example the drug may be stored between a distal seal and a proximal seal.

Optionally the proximal seal may include a plunger seal inserted into the reservoir between the location of the drug and the proximal opening. For example the plunger seal may be free to slide along the reservoir. Optionally the distal seal may include a septum.

In some embodiments, a pushing assembly may include an expanding assembly. For example, an expanding assembly may include a telescoping screw and/or an expanding piston (for example driven by gas and/or fluid pressure).

Alternatively or additionally a pushing assembly may include a translating element and/or a linear actuator.

In some embodiments a coupler may unseal an opening in a reservoir and/or supply a connection between the reservoir and a fluid path in the delivery device. For example, an opening in the reservoir may be sealed by the septum. The coupler optionally includes a hollow needle sharpened on a first end. For example the needle and/or reservoir may be united by a longitudinal movement to pierce the septum with the first end of the needle. Optionally the second end of the needle is connected to a flow path of the delivery device.

For example the needle may supply a connection for fluid to flow from the reservoir to a fluid path. Alternatively or additionally, the coupler may include a septum pierced by a needle of the cartridge. Alternatively or additionally other type connectors may be included, for example a slip lock and/or luer lock. In some embodiments the coupler may be connected to the cartridge by a user action, for example inserting the cartridge into the device. For example inserting the cartridge into the device may cause a needle to puncture a septum. Alternatively or additionally, the coupler may be connected to the cartridge during by an action of another component of the device and/or as part of the order of functioning of the device. For example, force of an actuator, for example the pushing assembly, may force the cartridge into connection with the coupler. Alternatively or additionally, the coupler may be moved to connect to the cartridge.

In some embodiments a compartment of the delivery device may retain a cartridge in functional connection to a coupler and/or a pushing assembly. For example, the chamber may align the axis in a desired direction and/or may position the cartridge in a desired location. For example, the chamber may facilitate insertion of the cartridge in a particular orientation and/or into a particular position. For example the compartment may include an element that directs the cartridge and/or fits the cartridge (for example a tapered pin and/or a tapered opening). Alternatively or additionally a compartment may include an element that forces a cartridge into a desired position and/or orientation (for example an elastic element may push a cartridge to a desired position). Alternatively or additionally a compartment may include a retaining element (for example a clip and/or a latch) which holds the cartridge in place.

In some embodiments a cartridge and/or reservoir may be positioned in a compartment by sliding longitudinally into the compartment. Alternatively or additionally a first side of the cartridge and/or reservoir may be placed into the compartment and then the cartridge and/or reservoir may be rotated to position the second end in the compartment. Alternatively or additionally, the cartridge and/or reservoir may be positioned in the compartment by inserting laterally into the compartment. Optionally the cartridge and/or reservoir may be placed into a bay and positioned into the compartment with the bay.

For example a bay may tilt into the compartment and/or rotate and/or slide laterally or longitudinally into the comportment.

In some embodiments a drug delivery device may include a drug administration interface. Optionally a drug administration interface may include a skin contact surface. Alternatively or additionally, the drug administration interface may include an injection device. For example, an injection device may inject a drug under one or more layers of the skin of a user. For example an injection device may include a needle and/or a needle free injector, for example a jet injector.

In some embodiments, a longitudinal axis of a fluid reservoir (for example the longitudinal axis of a cylindrical portion of a cavity) will substantially be parallel to a skin contact surface. For example the angle between the longitudinal axis of the reservoir and the skin contact surface may range between 0 to 5 degrees and/or between 5 to 15 degrees and/or between 15 to 30 degrees and/or between 30 to 60 degrees. Optionally an injection device may have an axis (for example the longitudinal axis of a needle and/or the direction of a fluid jet). Optionally the axis of an injection device may be substantially perpendicular to the longitudinal axis of the reservoir. Additionally or alternatively, the angle between the axis of an injection device and the longitudinal axis of the reservoir may range between 90 to 85 degrees and/or between 85 to 70 degrees and/or between 70 to 30 degrees. In some embodiments a skin contact surface may not be flat. For example the axis of the reservoir may be parallel to the skin contact surface at a point on the surface in the vicinity of a needle hole and/or an injection location and/or at a point nearest to the center of the reservoir and/or in the vicinity of the axis of the reservoir.

In some embodiments a cartridge may fit a channel and/or a cartridge and/or a cartridge bay may exactly fit into a compartment of a delivery device (for example there may be tolerance of less than 0.1 mm and/or between 0.1 to 0.5 mm and/or between 0.5 to 1 mm and/or between 1 to 3 mm. Alternatively or additionally the compartment may be longer than the cartridge and the coupler. For example, the space between the pushing assembly and the cartridge may be between 3 to 5 mm greater than the length of the cartridge and/or 5 to 10 mm greater. For example the cartridge may be inserted into the compartment without connecting the coupler to the cartridge. After positioning the cartridge in the compartment, the pushing assembly may push the cartridge into the coupler and/or connect the reservoir to the coupler.

Optionally, a channel may be sized and shaped such that the distal opening of the reservoir faces the coupler.

For example, when the distal end of the cartridge is fully inserted into the channel, the distal opening of the reservoir may contact the coupler and/or the couple may form a flow path through the distal opening of the reservoir. For example, the channel may be sized and shaped to prevent the cartridge from twisting and/or rotating around in such a way that the distal opening of the reservoir would not contact and/or connect and/or be directly proximal to the coupler. For example the channel may fit the sides of the cartridge with high precision. Optionally, a channel may be sized and shaped so that the proximal opening of the reservoir faces the expanding assembly. For example, the channel may align the distal opening of the reservoir with the expansion axis of the expanding assembly such that distal expansion of the assembly moves the distal end of the assembly into the reservoir.

Optionally, the drug delivery device includes a compartment that retains the cartridge during drug delivery and/or a stopper pushing assembly mounted behind (proximal to) the compartment. In some embodiments, the cartridge may be inserted laterally into the compartment in front of (distal to) the pushing assembly.

In some embodiments, the delivery device may include a moving cartridge bay. The cartridge is optionally inserted into the bay while the bay is in a loading position. Subsequently the bay and cartridge optionally move into a delivery position, for example in the cartridge compartment. For example the cartridge may be loaded into the bay while the axis of the reservoir is not coaxial with the pushing assembly.

Subsequently, the bay and cartridge may be moved into the compartment and/or into alignment with the pushing assembly. For example, the bay may move laterally and/or rotate into the compartment. Optionally in the loading position a proximal opening of the bay is positioned outside the cartridge compartment of the drug delivery device.

In some embodiments, the cartridge compartment may have a proximal opening into which the cartridge is inserted. Optionally, the pushing assembly may be moved into position behind the proximal opening after insertion of the cartridge.

In some embodiments the cartridge may be sealed. Optionally a seal may be broken by a longitudinal movement. For example, a cartridge may include a seal (for example a septum) on a front (distal) end of the cartridge. The seal is optionally punctured by inserting a cannula axially through the front of the cartridge.

For example, the cannula may be mounted to a cartridge bay and/or a distal opening of the cartridge may be unsealed by longitudinally inserting a distal portion of the cartridge into the bay. The bay and the cartridge may be moved laterally into the cartridge compartment.

Alternatively or additionally, the seal may be punctured by a cannula located in the housing of the delivery device. For example, the seal may be punctured when the cartridge is inserted into the compartment. For example the cartridge may be inserted longitudinally into a proximal opening of the cartridge compartment.

Alternatively or additionally subsequent to insertion the seal may be broken.

For example, the plunger driving assembly may push the cartridge distally into the cannula, puncturing the cartridge seal.

In some embodiments, the cartridge is fully loaded to the bay and/or connected to the coupler while the bay is in the loading position. For example, when the cartridge is fully loaded while the bay is in the loading position, the proximal opening of the reservoir is outside the cartridge compartment and/or a portion the reservoir is outside of the compartment, for example between 5 to 15% and/or between 15 to 40% and/or between 40 to 80% and/or between 80 to 100% of the reservoir. For example the portion of the reservoir outside the compartment may be defined as the portion of the drug contained in the reservoir that is outside the compartment.

In some embodiments, the pushing assembly may include a telescoping assembly (TSA) and/or a linear and/or a rotational stabilizer. For example a rotational stabilizer may be mounted to a housing of the drug delivery device and/or a motor mount such that torque on the final element of the telescoping assembly that pushes the stopper is balanced against the motor and/or the housing of the delivery device.

Optionally the torque will not be applied to the drug reservoir and/or the stopper and/or any component that is in contact with the drug.

In some embodiments a cartridge pushing assembly may be positioned behind to a proximal opening of the drug cartridge without regard to the precise longitudinal position of a stopper in the cartridge. Optionally, after positioning the stopper pushing assembly and/or the cartridge, the TSA may be extended until the pushing assembly contacts the stopper. For example, the TSA may be extended after inserting the cartridge into the drug delivery device and/or after positioning the TSA behind the cartridge.

In some embodiments, the stroke length of the TSA may be greater than the minimum length of the TSA.

For example a TSA may have three or more telescoping shafts and/or one or more telescoping guides. For example a telescoping shaft may include an extension rod. Alternatively or additionally a TSA may have four telescoping shafts and/or one, two or more telescoping guides. Alternatively or additionally a TSA may have five telescoping shafts and/or two, three or more telescoping guides. For example a TSA may have a contracted configuration with length ranging between 0.8 and 1.6 cm and/or between 1.6 to 3.2 cm. For example a TSA may have an extended configuration with length ranging between 2.0 to 6.0 cm and/or between 6 to 12 cm.

Optionally, the extended length of the TSA may range between 2.0 to 3.0 times the contracted length and/or between 3.0 to 5.0 times the contracted length.

Before explaining at least one embodiment of the invention in detail, it is to be understood that the invention is not necessarily limited in its application to the details of construction and the arrangement of the components and/or methods set forth in the following description and/or illustrated in the drawings and/or the Examples. The invention is capable of other embodiments or of being practiced or carried out in various ways.

Cartridge Insertion Assembly

Referring now to the drawings, FIG. 1A is a block diagrams of a cartridge inserted into a cartridge bay in a loading position in accordance with an embodiment of the present invention. In some embodiments, a cartridge bay 123 is movably connected to the delivery device (for example a housing 122a of the delivery device) by a multi-position mount 125 (for example including a pivot and/or a slider and/or a hinge). Optionally the bay includes a coupling 148 connecting a reservoir 120 of drug cartridge 153 to a fluid path 149 of the delivery device. Optionally, all or part of cartridge 153 is loaded to bay 123 while bay 123 is in the loading position. For example when the cartridge 153 is loaded into the bay, cartridge 153 may be connected to coupling 148. Optionally while bay 123 is in the loading position all or part of bay 123 is located outside of a housing of the delivery device. For example, in the loading position between 100% to 75% and/or between 75% to 50% and/or between 50% to 25% and/or between 25% to 5% of bay 123 and/or cartridge 153 may be outside of the delivery device and/or housing 122a and/or a cartridge compartment of the delivery device. Alternatively or additionally, bay 123 may include a proximal opening for loading cartridge 153 to bay 123. In the loading position, the proximal is optionally clear of the delivery device.

In some embodiments, cartridge 153 includes a drug reservoir 120. For example reservoir 120 may include a proximal opening 141 and/or a distal opening.

Optionally an opening may be closed by a seal 146, for example a septum. While loaded into bay 153 in the loaded position, opening 141 may be free of the and/or outside of the delivery device. Reservoir 120 may contain a drug. For example the drug may be sealed between stopper 140 and seal 146.

In some embodiments, coupling 148 may include a cannula. When cartridge 153 is loaded into bay 123, the cannula is optionally inserted through a septum of seal 146 providing fluid communication between drug 144 and fluid path 149. Optionally coupling 148 is mounted to and/or moves with bay 123. Optionally, coupling 148 is mounted to housing 122a. Optionally, fluid path 149 keeps fluid communication open between coupling 148 and the delivery device for the different positions of bay 123.

For example, fluid path 149 may include a flexible tube. In some embodiments the cannula and/or fluid path may be in fluid communication with an injection needle.

In some embodiments, the delivery device may include a patch in injector.

Optionally in the distribution position, the long axis of the cartridge and/or the long axis of the cartridge compartment is substantially parallel to and/or at an angle of less the 10 degrees and/or between 10 and 30 degrees to a base of the patch injector.

Optionally the base of the injector contacts the skin of a patient. Optionally the base of the injector may include an adhesive for adhering to the patient. In some embodiments an injection needle may be inserted into a patient. For example the injection needle may be inserted into the patient in a direction substantially perpendicular to the base and/or at an angle of between 85 to 90 degrees to the base and/or between 75 to 85 degrees to the base and/or between 60 to 75 degrees to the base.

In some embodiments the delivery device may include a stopper driving assembly 150. Driving assembly 150 is optionally fixedly mounted onto housing 122a proximal to a cartridge compartment. In the loading position, cartridge 153 and/or bay 123 may not be aligned with and/or couple to driving assembly 150.

Figure 1B:
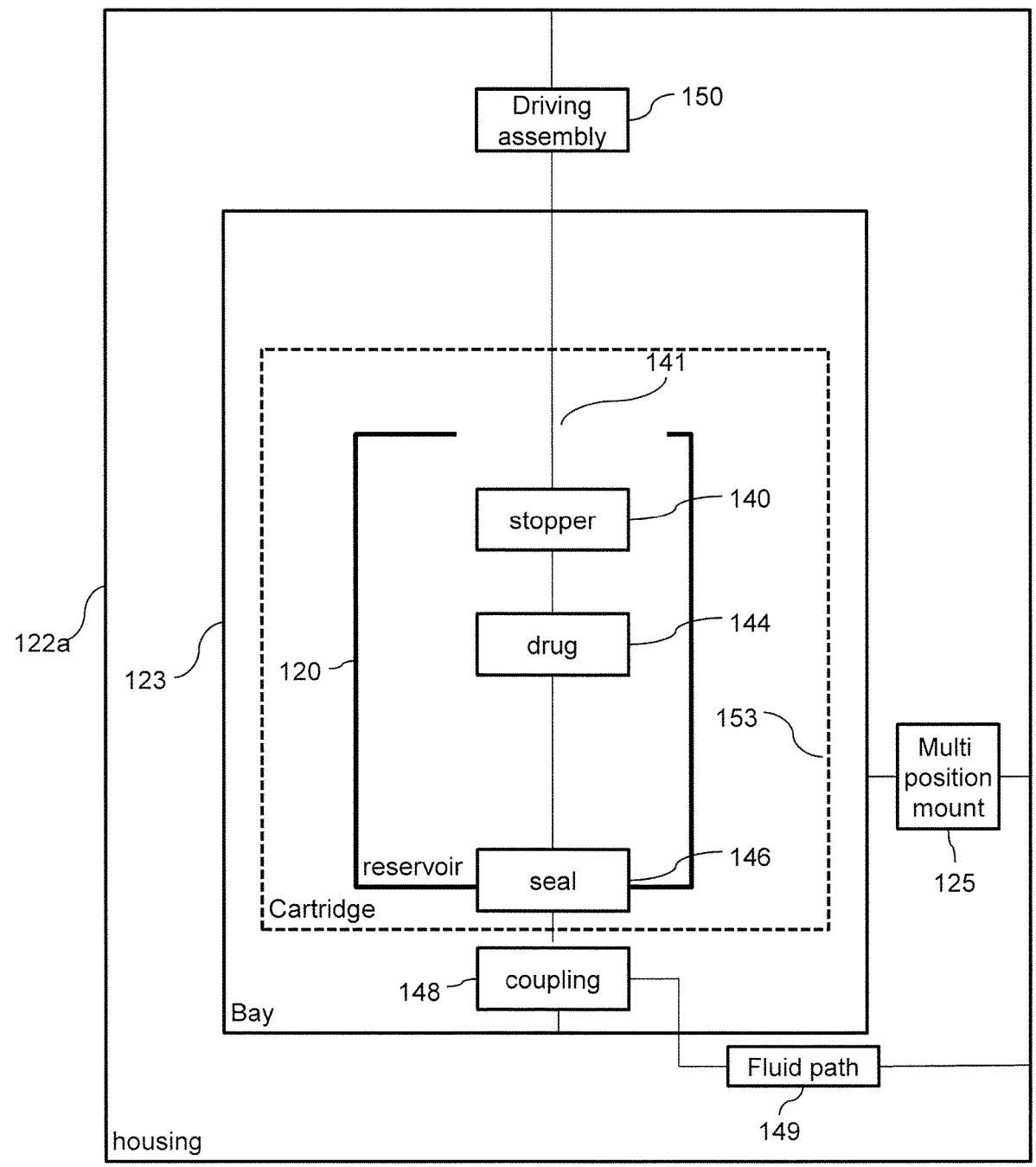
FIG. 1B is a block diagram of a cartridge insertion assembly with a moving cartridge bay in a delivery position in accordance with an embodiment of the present invention.

We refer now to the FIG. 1B which is a block diagram of a cartridge inserted into a cartridge bay in a delivery position in accordance with an embodiment of the present invention. In the delivery position, driving assembly 150 is optionally positioned proximal to cartridge 153 and/or opening 141. In the delivery position, driving assembly 150 is optionally aligned with opening 141 and/or engaged to stopper 140. For example, after positioning bay 123 and/or cartridge 153 in the delivery position, driving assembly 150 may advance a stopper interface to contact and/or push stopper 140 and/or discharge drug 144 through coupling 148 to fluid path 149.

For example, in the delivery position, between 100% to 75% and/or between 75% to 50% and/or between 50% to 25% and/or between 25% to 5% of bay 123 and/or cartridge 153 may be inside of the delivery device and/or housing 122a and/or the cartridge compartment.

Figure 1C:
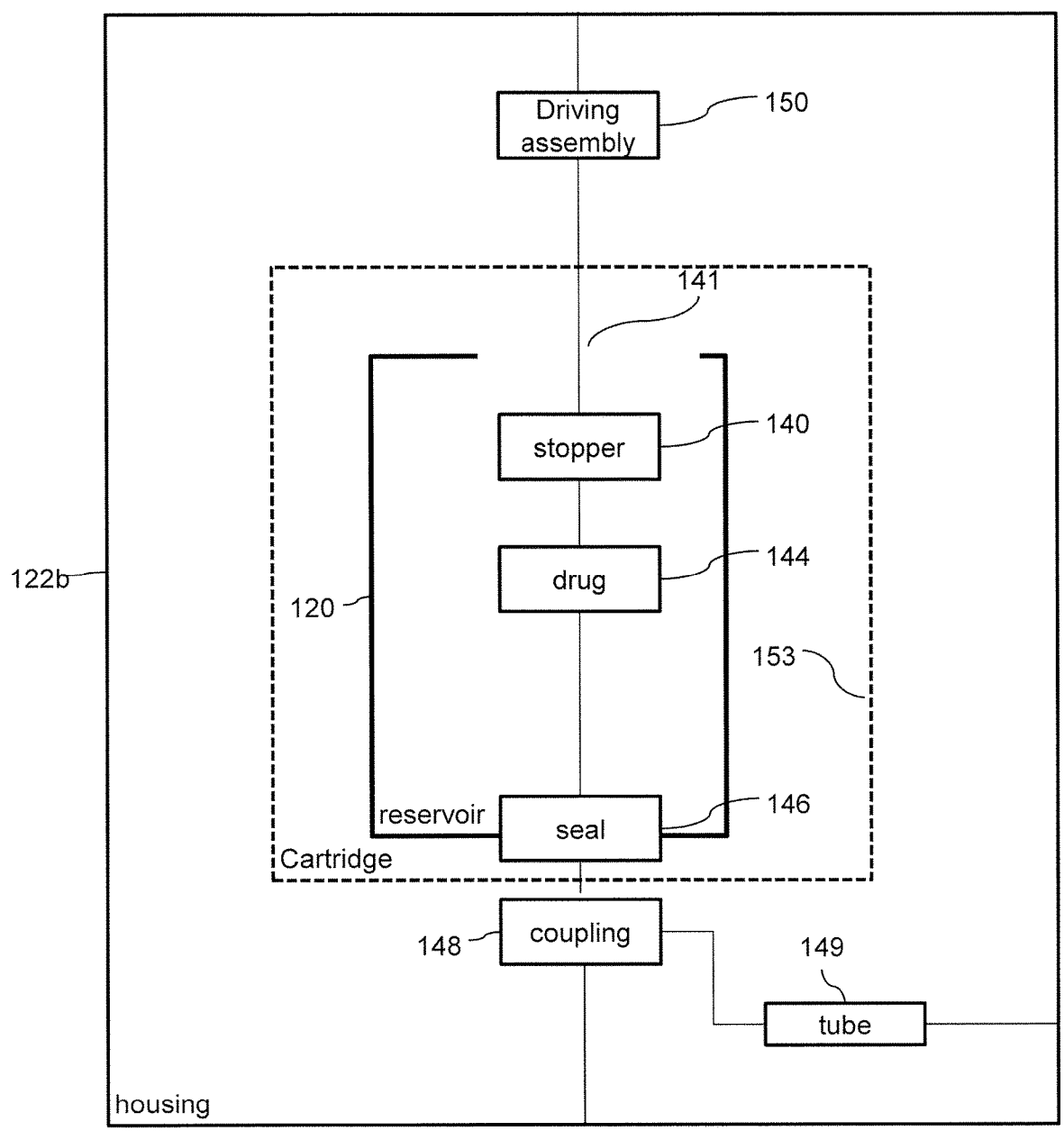
FIG. 1C is a block diagrams of a cartridge insertion assembly in accordance with an embodiment of the present invention.

We refer now to the FIG. 1C which is a block diagram of a cartridge inserted into a delivery device in accordance with an embodiment of the present invention. In some embodiments, coupling 148 may be mounted to a housing 122b of the delivery device. Optionally, housing 122b may include a proximal opening to a cartridge compartment. For example cartridge 153 may be inserted longitudinally into the proximal opening until coupling 148 engages the distal opening of reservoir 120 and/or pierces seal 146. Alternatively or additionally, housing 122b may have a side opening. For example, cartridge 153 may be inserted laterally into the side opening.

Optionally, driving assembly 150 may initially push cartridge 153 distally until coupling 148 engages the distal opening of reservoir 120 and/or pierces seal 146.

Figure 1D:
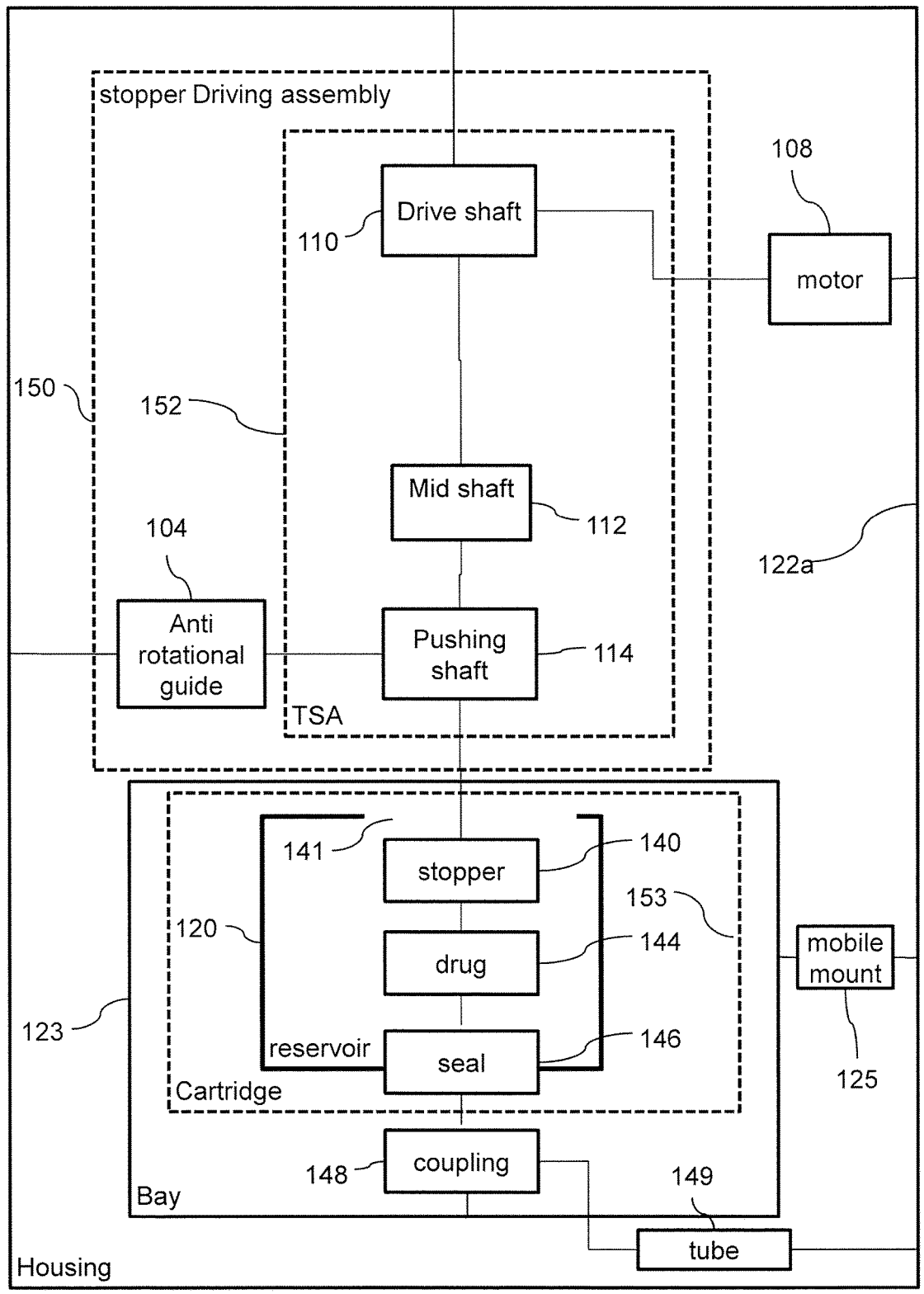
FIG. 1D is a block diagram of a drug delivery device and cartridge insertion assembly in accordance with an embodiment of the present invention.

We refer now to the FIG. 1D which is a block diagram of a cartridge inserted into a cartridge bay in a delivery position showing details of the plunger pushing assembly in accordance with an embodiment of the present invention.

Driving assembly 150 is optionally supported by housing 122b. For example, housing 122b may balance linear forces between driver assembly 150 and stopper 140 and/or cartridge 153. Driver assembly 150 optionally includes an anti-rotational guide, for example guide 104. Anti-rotational guide 104 optionally supports the driver assembly and/or balances torque between the driver assembly and a motor for example motor 108.

In some embodiments, stopper driver assembly 150 may include a telescoping assembly (for example TSA 152).

Optionally, TSA 152 includes a proximal shaft, for example a threaded drive shaft 110 and/or a threaded mid shaft 112 and/or a distal shaft, for example a threaded pushing shaft 114. Shafts 110, 112 and/or 114 may be coupled such that rotating drive shaft 110 with respect to pushing shaft 114 causes TSA 152 to lengthen and/or shorten. Optionally axial movement of drive shaft 110 is limited by linear stabilizer 106 such that rotating drive shaft 110 with respect to pushing shaft 114 causes pushing shaft 114 to move linearly with respect to linear stabilizer 106. Optionally, a coupling links guide 104 and/or pushing shaft 114 to housing 122b. For example, rotation of pushing shaft 114 may be limited by housing 122b such that rotating drive shaft 110 with respect to housing 122b causes TSA 152 to lengthen and/or shorten.

Alternatively or additionally, drive shaft 110 and/or pushing shaft 114 may be replaced by a nut and/or threaded disk and/or ring.

In some embodiments motor 108 may include a DC electric motor, a chemical engine, a brushless motor, an AC motor, an actuator etc.

In some embodiments, linear stabilizer 106 and/or housing 122b may be attached to drug cartridge 153 and/or pushing shaft 114 may abut against stopper 140 such that extending TSA 152 moves stopper 140 axially with respect to reservoir 120.

Axial back forces of stopper 140 with respect to reservoir 120 (for example due to friction between stopper and the walls of the reservoir and/or due to flow resistance) are optionally balanced against linear stabilizer 106 and/or housing 122b.

In some embodiments, motor 108 may apply a torque to drive shaft 110.

Optionally, anti-rotational guide 104 may be attached to drug cartridge 153 such that activating motor 108 moves pushing shaft 114 axially with respect to drive shaft 110. Friction between driving shaft 110, mid shaft 112, and/or pushing shaft 114 are optionally balanced by an anti-torque between motor 108 guide 104 and/or housing 122b such that TSA 152 acts as a linear actuator putting a net linear force (and/or a negligible torque) on the parts of the device that are in contact with the drug (for example stopper 140 and/or cartridge 153).

In some embodiments, mid-shaft 112 and/or anti-rotational guide 104 may move axially. For example mid-shaft 112 and/or anti-rotational guide 104 may move into and/or out of reservoir 120. For example guide 104 may be slidably and/or anti-rotationally connected to housing 122b for example by a track.

In some embodiments, the order of movement of parts of TSA 152 may be not fixed.

For example, in some embodiments, mid shaft 112 is free to rotate along with driving shaft 110 and/or rotate along with pushing shaft 114. For example, the position of some part (for example mid shaft 112) may be indeterminate in some configurations (for example when TSA 152 is partially extended). For example the part may move without changing the length of TSA 152.

In some embodiments, guide 104 may slide and/or anti-rotationally connect to housing 122b. For example the connection may include a longitudinal track. Pushing shaft 114 may slide and/or be anti-rotationally connected to guide 104 for example by a longitudinal track.

In some embodiments, driver shaft 110 may be an inner shaft and the pushing shaft 114 may be an outer shaft. Alternatively or additionally driver shaft 110 may be an outer shaft and the pushing shaft 114 may be an inner shaft. Any or all of the components of the current invention may be made of plastic and/or metal and/or another material.

Drug Delivery Device

Figure 2A:
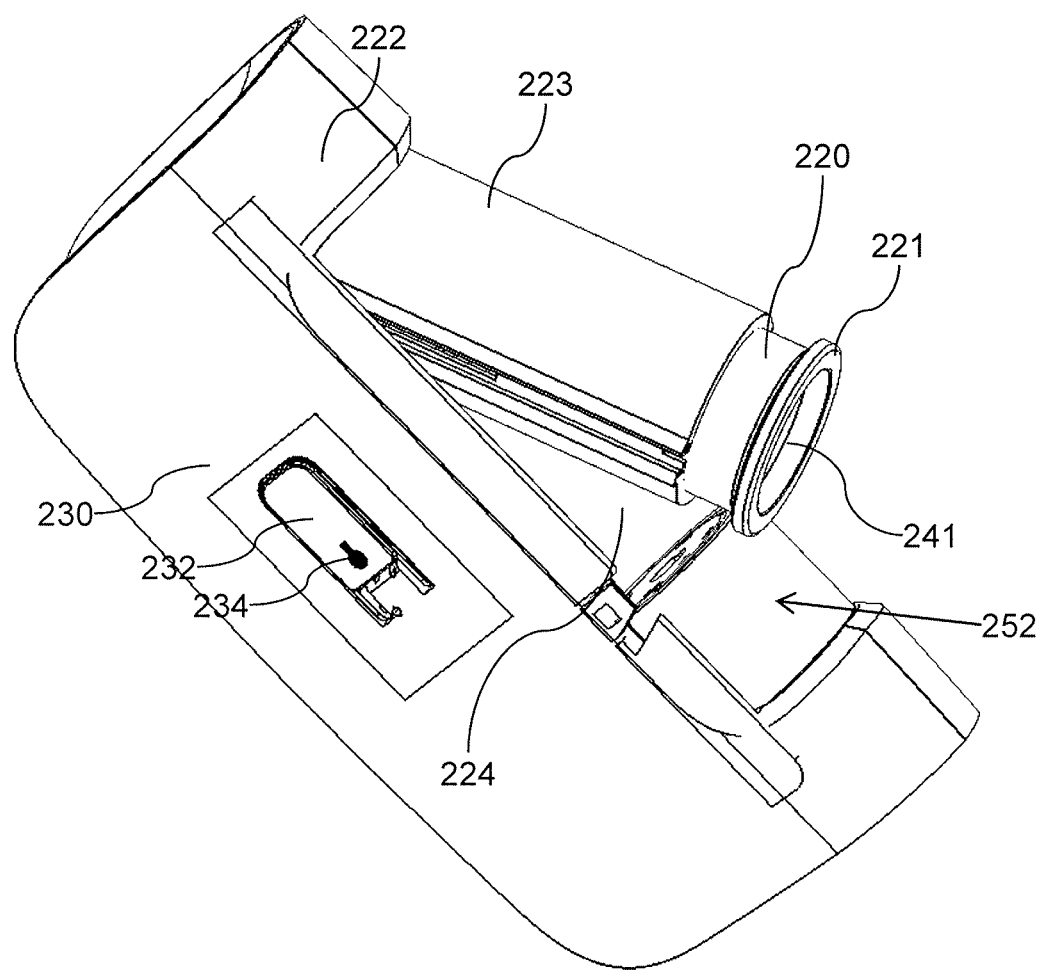
FIGS. 2A-B illustrate an exemplary drug delivery device in accordance with an embodiment of the present invention.
Figure 2B:
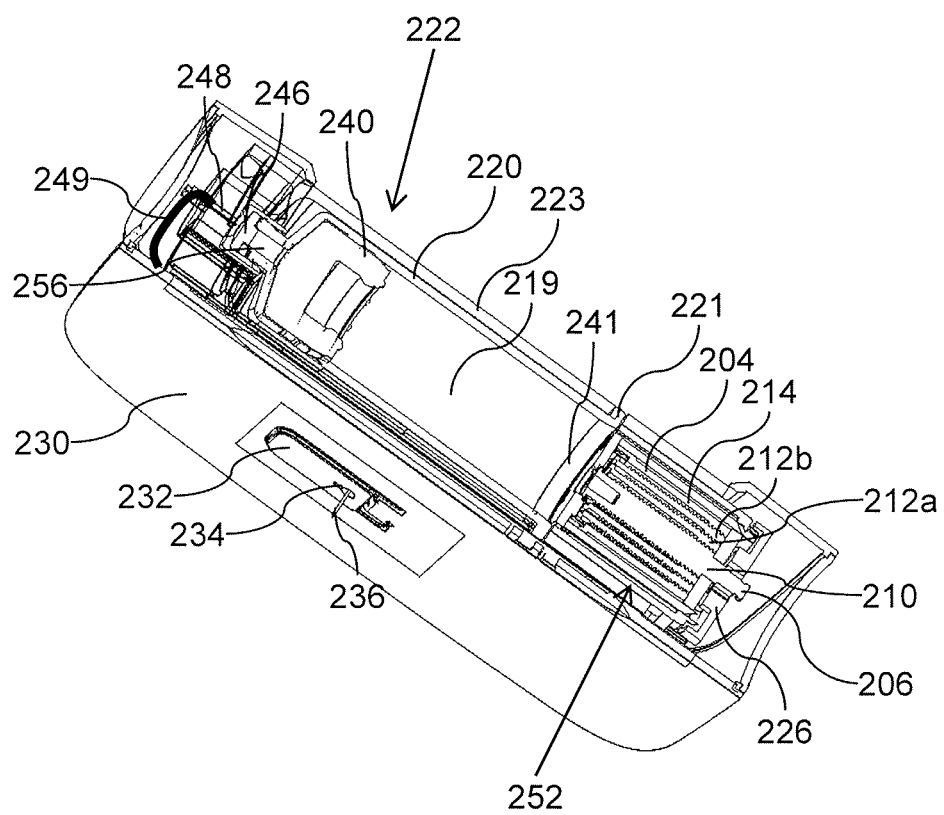

FIGS. 2A and 2B illustrate a drug delivery device in accordance with some embodiments of the present invention. Optionally a drug delivery device includes a plunger pushing assembly and/or a fluid path coupler on opposing ends of a cartridge compartment. Optionally the cartridge compartment fits a drug cartridge with the axis of the cartridge reservoir parallel to a skin contact surface of the device.

FIG. 2A is a perspective view of a drug delivery device 222 and a cartridge 220 In accordance with an exemplary embodiment of the current invention. In some embodiments drug delivery device 222 may include a cartridge compartment 224.

Optionally, compartment 224 is sized to fit cartridge 220. For example cartridge 220 fits into compartment 224 snugly between a piston pushing assembly 252 and a coupler (for example including a coupler may include a hollow needle 248 as illustrated for example in FIG. 2B).

In some embodiments, cartridge 220 fits into compartment 224 inside a cartridge bay 223. Optionally, bay 223 opens out from compartment 224. For example, in the open position (for example as illustrated in FIG. 2A) cartridge 220 may be inserted into bay 223. For example, to position cartridge 220 into compartment 224 a user may insert cartridge 220 into bay 223 in the open position and then close bay 223; thereby 220 into compartment the inserting cartridge.

Optionally bay 223 opens and/or closes by pivoting into and/or out of compartment 224.

In some embodiments a drug delivery device 222 may include an administration interface. For example, device 222 includes a skin contact surface 230.

For example, when delivering a drug, skin contact surface 230 is placed against the skin of a user. Optionally, all or part of skin contact surface 230 is coated with an adhesive.

For example the adhesive may hold the device to a user during drug delivery.

Optionally skin contact surface 230 includes a needle shield 232 and/or a drug delivery hole 234.

For example, a needle may be extended out of hole 234 into the skin of a user and/or a drug may be discharged through the needle and/or through hole 234 into the user. Optionally after use, shield 232 may extend to cover the needle and/or to prevent a stick hazard. Alternatively or additionally, a needle may retract into device 222 after drug discharge, for example to prevent a stick hazard. Alternatively or additionally a drug delivery device may include a jet injector and/or other injection device.

FIG. 2B is a cutaway view of injector 222 in accordance with an embodiment of the current invention. In FIG. 2B, cartridge 220 is illustrated positioned inside compartment 224. Optionally, cartridge 220 includes a cylindrical reservoir 219. For example, when positioned inside compartment 224, the longitudinal axis of cylindrical reservoir 219 is parallel to skin contact surface 230. In exemplary injection device 220, an injection needle 236 is illustrated in an extended position. Optionally, needle 236, in the extended position, is perpendicular to the longitudinal axis of reservoir 219. Optionally a fluid path, for example including a flexible tube 249, connects needle 236 to a coupler. For example, the coupler may include a hollow needle 248. Optionally, needle 248 of the coupler is mounted to device 222 at one end of compartment 224. Optionally, piston pushing assembly 252 is mounted to device 222 at an opposing end of compartment 224. When cartridge 220 is loaded into device 222, it is optionally placed between piston pushing assembly 252 and the coupler. Optionally, piston pushing assembly 252 expands along an axis of expansion that is coaxial to cartridge 220 when cartridge 220 is positioned inside compartment 224.

In some embodiments a coupler includes a hollow needle 248. For example needle 248 opens a fluid communication between fluid path 249 and reservoir 219.

For example, when cartridge 220 is inserted into bay 223, a septum 246 is pierced by needle 248.

In some embodiments, needle 248 may pierce septum 246 after cartridge 220 is positioned inside compartment 224. For example, piston pushing assembly 252 may push cartridge 220 longitudinally into needle 248. For example, compartment 224 may be slightly longer than cartridge 223. Optionally the needle may penetrate the septum for example between 1 to 3 mm and/or between 3 to 6 mm and/or between 6 to 12 mm. Optionally, the cartridge may move between 1 to 3 mm and/or between 3 to 6 mm more than the needle penetration. For example the compartment may be 3 to 6 mm and/or 6 to 12 mm longer than the cartridge.

In some embodiments, cartridge 220 may include a syringe. For example, a syringe may include a cylindrical reservoir 219. Reservoir 219 optionally includes a cylindrical cavity having a distal opening 256 and/or a proximal opening 241.

Optionally, the distal portion of reservoir 219 is filled with a drug.

In some embodiments, a plunger seal 240 is inserted into reservoir 219. For example, the plunger seal 240 may seal reservoir 219 between the location of the drug and proximal opening 241. Optionally the syringe may include a proximal flange 221. For example, flange 221 may facilitate positioning and/or retaining the syringe in bay 223 and/or compartment 224. Alternatively or additionally, syringe 220 may be filled in an automated filling machine. For example, flange 221 may be used by the filling machine for handling and/or positioning the syringe. For example, the syringe of cartridge 220 may be a standard size and/or shape that fits into a standard filling machine. In some embodiments, opening 256 is coaxial to reservoir 219.

Alternatively or additionally, opening 256 may be positioned eccentrically with respect to reservoir 219.

Optionally, piston pushing assembly 252 includes a telescoping screw assembly.

For example, piston pushing assembly 252 includes a driver 210 that is optionally rotated by a transmission and/or a motor. For example a transmission may include a gear 226. Optionally the transmission and/or driver and/or motor remain permanently engaged. For example the transmission and/or motor and/or driver may remain engaged before insertion of the cartridge, during insertion of the cartridge and/or after insertion of the cartridge into the compartment of the device.

Driver 210 is optionally supported from a distal end by a linear stabilizer, for example, a bearing 206 pushing against a housing of device 222. Optionally, driver 210 is threadably connected by two mid screws 212a and 212b and/or to a plunger driver 214.

For example, plunger driver 214 may be allowed to move longitudinally with respect to driver 210 and/or prevented from rotating with respect to the housing of device 222, for example by an anti-rotational guide 204. For example, rotating driver 210 causes relative rotation of threaded parts, for example driver 210, mid screws 212a, 212b and plunger driver 214 and/or longitudinally extension of piston pushing assembly 252. For example, plunger driver 214 may be driven along the axis of reservoir 219 and/or into reservoir 219. As plunger driver 214 moves into reservoir 219 it optionally pushes plunger seal 240 distally and/or drives the drug out of the opening in septum 246 and/or through needle 248 and/or into fluid path 249 and/or through needle 236 and/or into a user. In some embodiments, piston pushing assembly 252 drives plunger driver 214 to into opening 241. For example, plunger driver 214 may move into opening 241 until it engages and/or contacts plunger seal 240. Optionally, further expansion of piston pushing assembly 252 after plunger driver 214 engages plunger seal 240 drives plunger seal 240 distally into reservoir 219.

Optionally driving plunger seal 240 distally into the reservoir 219 causes discharge of the drug for example through distal opening 256 of reservoir 219.

Filling a Cartridge

In accordance with some embodiments of the present invention, a reservoir may be fillable with standard pharmaceutical equipment (for example in an existing clean room with filling equipment made for a standard syringe and/or cartridge).

Optionally, the stopper driver engages the stopper located at an arbitrary position within the reservoir. In some embodiments the stopper driver may be assembled with snap together parts. The parts are optionally made of molded materials such as plastic, for example polyoxymethylene (POM) resin.

In some embodiments a drug reservoir is supplied. Optionally the reservoir may be prefilled. For example, the reservoir may be filled using standard filling equipment. For example, the reservoir may have a cylindrical and/or tubular bore or cavity and/or a bore of arbitrary cross section. For example the body may be in the form of a right circular cylinder. Optionally, the internal cavity may be of arbitrary shape. For example, the internal cavity may have a smooth wall over at least half its length and/or over at least 90% of its length. For example the cavity of the reservoir may be substantially a right circular cylinder over at least half its length and/or over at least 90% of its length. For example the internal cavity may be coaxial with the outer walls of the cartridge over at least half its length and/or over at least 90% of its length.

For example the cross section of the cavity may be uniform over at least half its length and/or over at least 90% of its length. Optionally the reservoir may include a distal opening.

In some embodiments, a distal portion of the reservoir may include cannula for example a hypodermic needle and/or a mount for such. Alternatively or additionally the distal portion of the reservoir and/or the distal opening may include a seal, for example a septum and/or sterile cover for example a needle cover. The proximal end of the reservoir may include a proximal opening. Optionally the proximal opening may be larger than the distal opening. For example the cross sectional area of the proximal opening may range between 5 to 50 times the cross sectional area of the distal opening and/or 50 to 500 times the cross sectional area of the distal opening. Optionally, an opening may be beveled and/or may smoothly connect to the internal cavity of the reservoir. Optionally, a stopper may be inserted into the proximal opening. Optionally, a plunger seal, for example a stopper may seal and/or preserve sterility of the contents of the reservoir. Optionally the position of the stopper may vary dependent on the volume of the contents of the reservoir. Optionally the proximal end of the cartridge may include a flange. For example the flange may extend from the between 20% to 100% of the perimeter of the cartridge. For example the flange may extend between 1 mm and 2 cm from the internal walls of the proximal opening. Optionally the reservoir may be made as a single integral unit for example of molded glass or plastic and/or cut and/or processed tubing.

Insertion of a Drug Cartridge

Figure 3A:
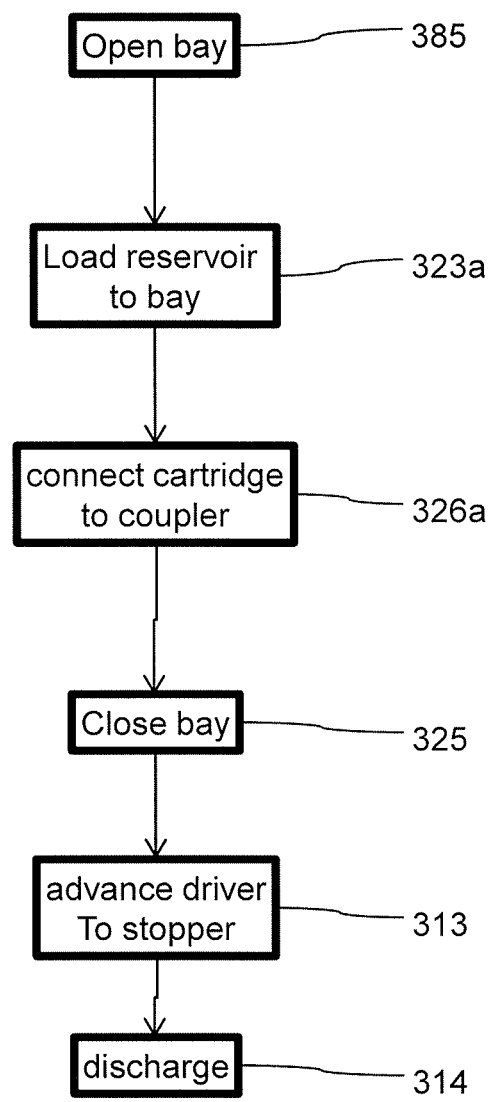
FIG. 3A is a flow chart illustrating a method of cartridge insertion in accordance with an embodiment of the present invention.

FIG. 3A is a flow chart illustrating a method of cartridge insertion in accordance with an embodiment of the present invention. For example, the cartridge may be inserted with a moving bay. For example, the bay may be opened 385 to a loading position. With the bay in a loading position, the cartridge and/or a portion thereof is optionally loaded 323*a* to the bay. For example, the bay may include a proximal opening and/or a distal portion of the cartridge may be inserted longitudinally into the bay for example through the proximal opening thereof. For example between 1 to 5% of the cartridge may be inserted into the bay and/or between 5 to 15% of the cartridge may be inserted into the bay and/or between 15 to 40% of the cartridge may be inserted into the bay and/or between 40 to 75% of the cartridge may be inserted into the bay and/or between 75 to 100% of the cartridge may be inserted into the bay. In some embodiments, inserting the cartridge into the bay may connect 326*a* a coupler to the cartridge. For example, the bay may include a cannula that protrudes proximally into the distal end of a cartridge channel in the bay.

When the cartridge is inserted into the channel, the cannula optionally pierces a septum on a distal end of the cartridge.

In some embodiments, with the cartridge loaded 323*a* into the bay, the bay may be closed 325 to position the bay and/or the cartridge into a distribution position.

For example, the bay may slide or pivot into an opening in the side of the delivery device. When the cartridge is in the delivery position, the stopper pushing assembly may optionally be located proximal to the cartridge and/or aligned with a proximal opening in the drug reservoir and/or with the stopper.

In some embodiments, with the cartridge and/or bay in the closed 325 (e.g. in the distribution position), the stopper driving assembly may be advanced 313.

Extending the stopper driver may result in engagement of the stopper by a stopper interface and/or driving the stopper forward into the drug reservoir and/or discharging 314 the drug.

Figure 3B:
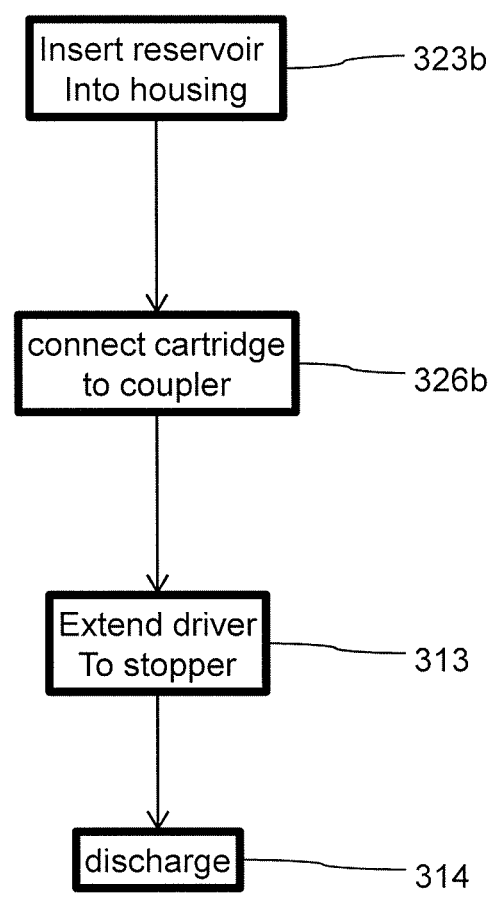
FIG. 3B is a flow chart illustrating a method of cartridge insertion in accordance with to an embodiment of the present invention.

FIG. 3B is a flow chart illustrating a method of cartridge insertion in accordance with an embodiment of the present invention. In some embodiments a cartridge may be inserted 323*b* laterally into the distribution device without a moving bay. Alternatively or additionally, the cartridge may be inserted 323*b* longitudinally into the device.

In some embodiments, the cartridge may be inserted 323*b* laterally into the delivery device. For example, the cartridge may be inserted 323*b* into an opening in the side of a housing of the device that leads to a cartridge compartment. Optionally after insertion 323*b*, a stopper driver is advanced 313 from behind the cartridge toward the stopper. The stopper driver optionally engages the stopper. The cartridge is optionally driven forward (for example by the stopper driver). For example, while the distal end of the cartridge is sealed, pressure on the plunger may not drive a discharge the drug. The pressure on the stopper and/or the fluid pressure optionally drive the cartridge forward. Driving the cartridge forward optionally connects 326*b* the drug reservoir to a coupler and/or forms a fluid pathway between the cartridge and the delivery device (for example by puncturing a septum). Opening a fluid path exiting the reservoir to the drug delivery device may facilitate advancement of the stopper inside the drug reservoir and/or discharge of the drug.

Further advance 313 of stopper driving assembly optionally advances the stopper into the drug reservoir and/or discharges 314 the drug. For example the drug may be discharged 314 through the coupler and/or into a fluid pathway of the delivery device and/or into a user. Alternatively or additionally, the syringe may be driven forward to connect to the coupler after insertion into the bay (for example while the bay is being closed to the delivery position and/or after the bay is closed to the delivery position) by a mechanism other than the expanding assembly, for example by a being pushed forward by an inclined surface.

In some embodiments the cartridge may be inserted 323*b* longitudinally into the device. For example the device may have a proximal opening leading to a cartridge compartment. The inserting 323*b* the cartridge longitudinally into the cartridge compartment optionally connects 326*b* the drug reservoir to a coupler and/or forms a fluid pathway between the cartridge and the delivery device (for example by puncturing a septum). Optionally, after the septum has been punctured, a stopper driver is advanced 313 from behind the cartridge toward the stopper. The stopper driver optionally engages the stopper. Further advance 313 of stopper driving assembly optionally advances the stopper into the drug reservoir and/or discharges 314 the drug. For example the drug may be discharged 314 through the coupler and/or into a fluid pathway of the delivery device and/or into a user.

Insertion Assembly with a Tilting Cartridge Bay

Figure 4A:
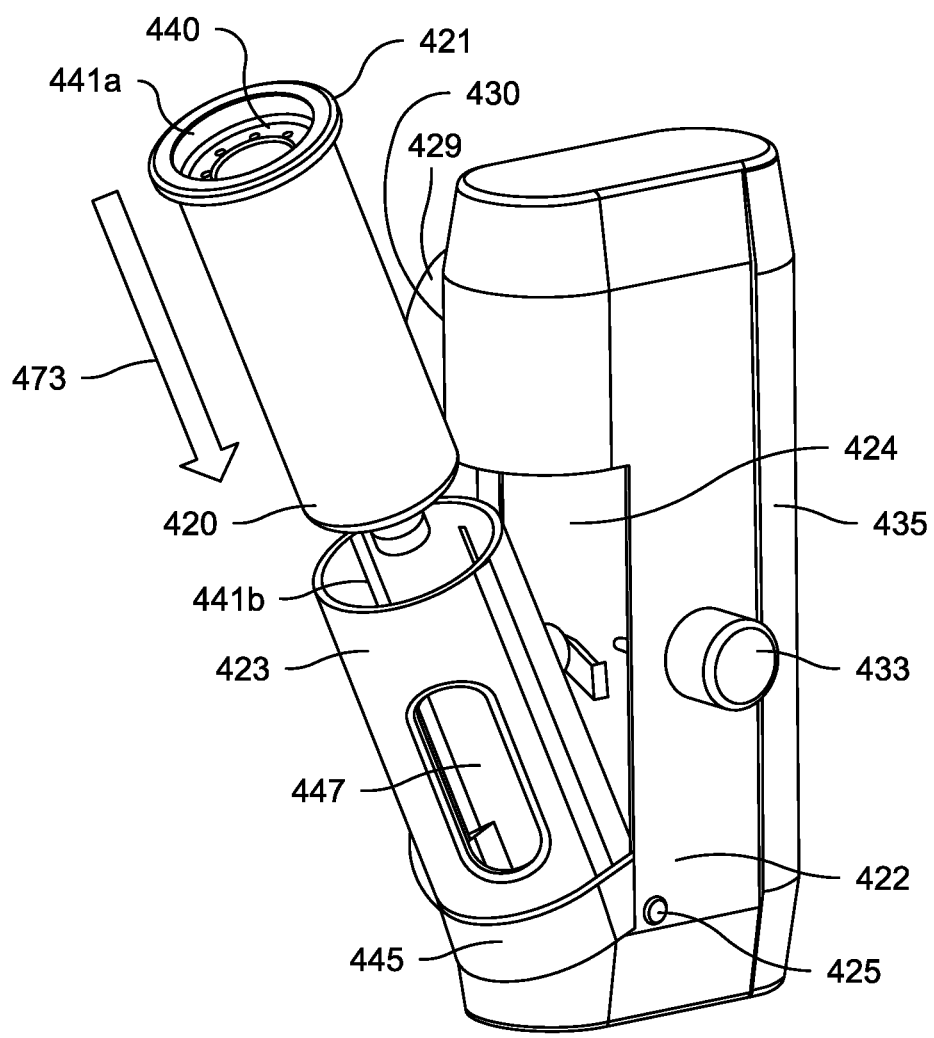
FIG. 4A is a perspective view of inserting a cartridge in accordance with an embodiment of the present invention.
Figure 4B:
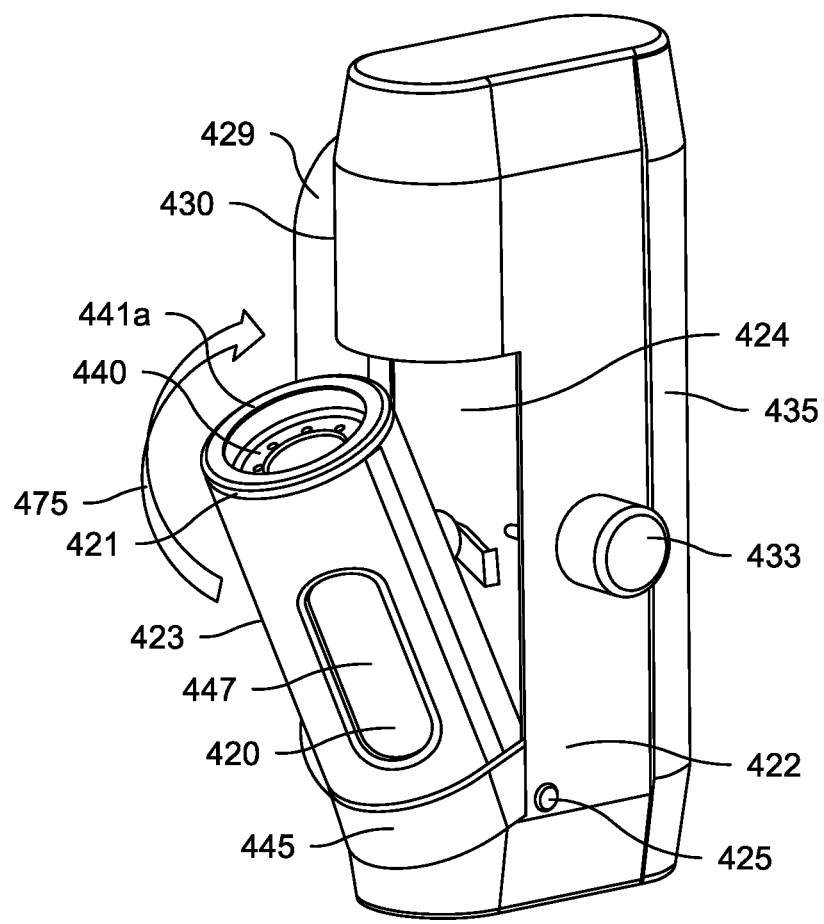
FIG. 4B is a perspective view of closing a tilting bay in accordance with an embodiment of the present invention.

FIG. 4A is a perspective view of inserting a cartridge into a tilting bay in accordance with an embodiment of the present invention. In some embodiments, a cartridge bay 423 tilts out of a drug delivery device 422 to a loading position for example as shown in FIG. 4A. Optionally bay 423 has a proximal opening 441*b* to a cylindrical channel (which can be seen for example through a window 447). The channel is optionally sized to fit a cartridge 420. For example cartridge 420 is illustrated optionally being inserted 473 through opening 441*b* into the channel. For example, bay 423 tilts along a movable, multiposition mount (for example a pivot 425). An optional support 445 supports bay 423 in the loading position. Optionally bay 423 and/or cartridge 420 rotate around pivot 425 into a closed position in a cartridge compartment 424, for example as illustrated in FIG. 4B. Optionally, in the closed position, cartridge 420 and/or bay 423 are coaxial with a plunger pushing assembly and/or compartment 424, for example as illustrated in FIG. 2B.

In some embodiments, cartridge 420 may include a standard syringe. For example, cartridge 420 may include a proximal opening 441*a*. A plunger seal 440 is optionally inserted through opening 441*a* to seal off a proximal portion of cartridge 420 from a drug included in a distal portion thereof. The distal end of reservoir optionally includes an opening 456 and/or a seal (for example a septum 446 for example as illustrated in FIG. 4D) and/or a needle mount. Optionally cartridge 420 includes a proximal flange 421.

In some embodiments delivery device 422 may include a patch injector. For example a skin contact surface 430 of the injector may be oriented parallel and/or nearly parallel to the long axis of cartridge 420. For example in FIGS. 4A-D, the skin surface base of the injector is facing into the page. The skin contact surface is optionally fully or partially covered by an adhesive 429 layer. Delivery device optionally includes an electronics compartment 435. Delivery device optionally includes an injection needle insertion assembly 433. For example after placing the skin contact surface onto the body of a patient, a user may push a protruding button of assembly 433 into the injector to release a needle outward from the skin contact surface into the patient.

FIG. 4B is a perspective view of a tilting bay in a loading position with a cartridge inserted in accordance with an embodiment of the present invention. In FIG. 4B cartridge 420 has optionally been inserted 473 into bay 423 and is visible through window 447. In the exemplary embodiment of FIGS. 4A-D, subsequent to insertion 473 of the cartridge into bay 423, bay 423 is optionally closed 475 by tilting into a cartridge compartment of delivery device 422.

Figure 4C:
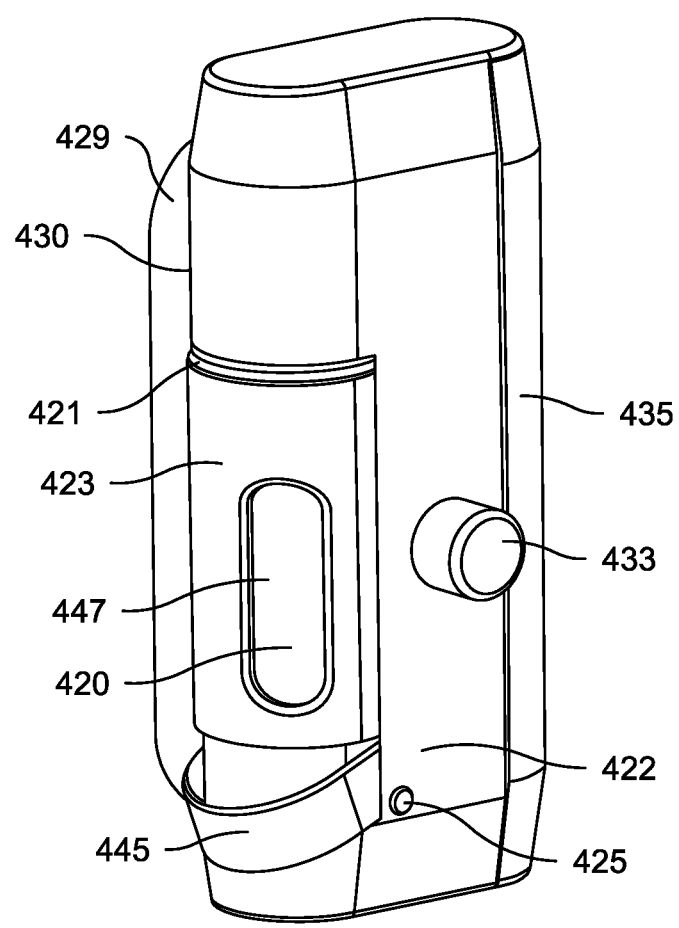
FIG. 4C is a perspective view of a closed tilting bay in accordance with an embodiment of the present invention.
Figure 4D:
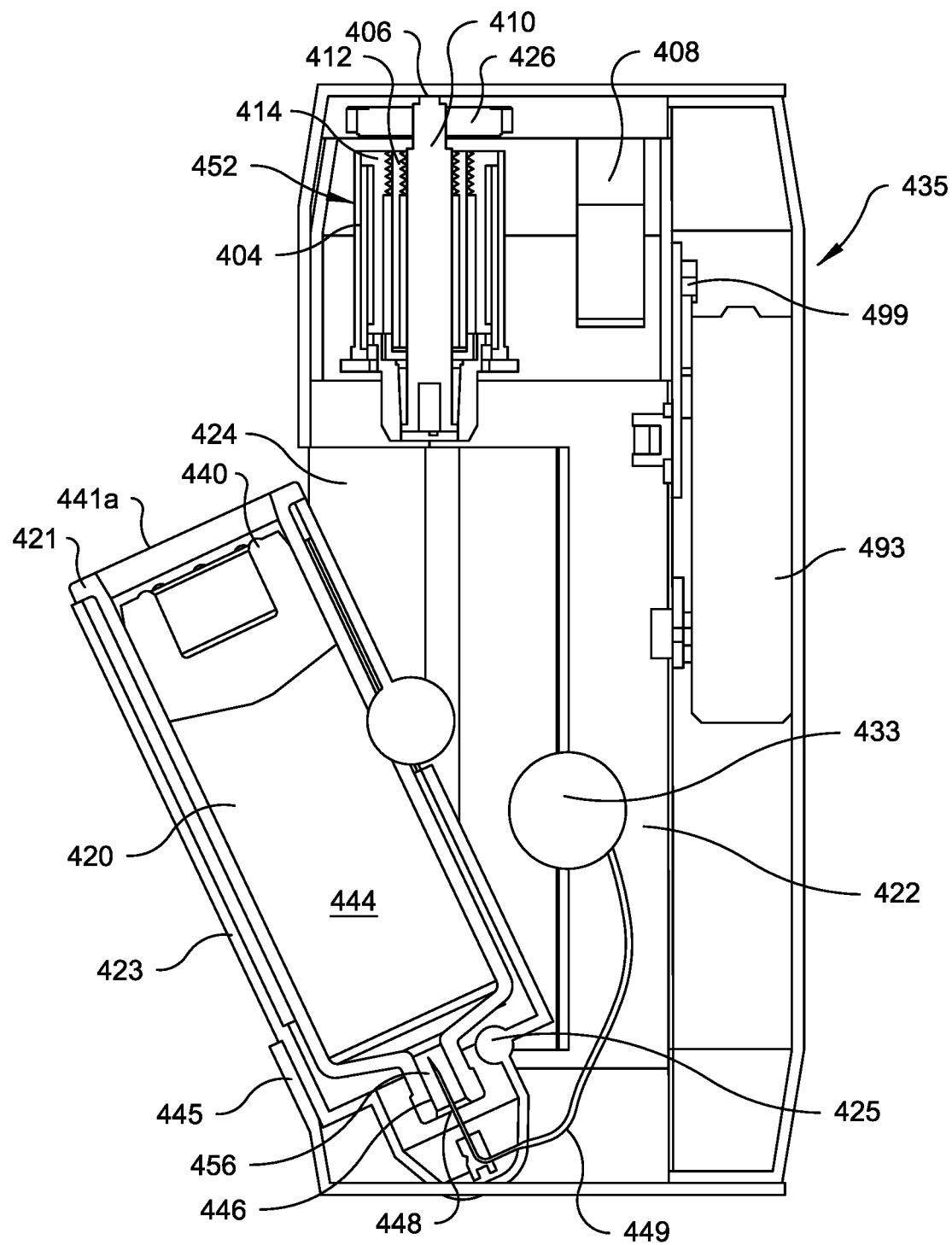
FIG. 4D is a cross sectional view of a drug delivery device and cartridge in accordance with an embodiment of the present invention.

FIG. 4C is a perspective view of a closed tilting bay in accordance with an embodiment of the present invention. Once the bay 423 is closed, a plunger driving assembly optionally located in the proximal end of device 422 proximal to opening 441a may drive plunger seal 440 distally and/or discharge the drug.

FIG. 4D is a cross sectional view of a drug delivery device with a tilting bay and cartridge in a loading position in accordance with an embodiment of the present invention. In FIG. 4D, an exemplary embodiment of a stopper driving assembly is illustrated. A stopper driver may include a TSA including for example an anti-rotational guide 404 and/or a stopper driver shaft 410 and/or a mid-shaft 412 and/or a stopper pushing shaft 414. Optionally guide 404 is connected to device 422 by a track that allows guide to slide linearly in a distal direction but prevents guide 404 from rotating with respect to device 422. Optionally, stopper driver shaft 410 is supported by a linear stabilizer, for example a bearing 406. For example, bearing 406 rests on the housing of device 422. Bearing 406 optionally allows stopper driver shaft 410 to rotate, but prevents stopper driver shaft 410 from moving proximally with respect to device 422.

In some embodiments, a transmission, including, for example, a gear 426 optionally connects stopper driver shaft 410 to a motor 408. Motor 408 optionally rotates stopper driver shaft 410 with respect to device 422. Rotating stopper driver shaft 410 with respect to device 422 while guide 404 optionally prevents stopper pushing shaft 414 from rotating with respect to device 422 optionally creates relative rotation between stopper driver shaft 410 and stopper pushing shaft 414. An optional set of screw threads mating stopper driver shaft 410, mid-shaft 412 and stopper pushing shaft 414 optionally translate relative rotation into linear telescoping of the assembly. Optionally the stopper pushing assembly is fixed in a proximal portion of device 422 and/or proximal to the cartridge compartment and/or proximal to the distribution position of cartridge 420. Electronics compartment 435 may include, for example, a power source (for example a battery 493) and/or a controller (for example a printed circuit board 499).

In some embodiments, in the loading position, the bay may pivot an angle of between 1 to 10 degrees and/or 10 to 30 degrees and/or 30 to 60 degrees and/or an angle between 60 to 90 degrees out of compartment 424.

In some embodiments, when cartridge 420 is inserted into bay 423 and bay 423 is closed and/or cartridge 420 is in the distribution position, distal advancement of stopper pushing shaft 414 pushes plunger seal 440 distally and/or discharges a drug 444 into a fluid path of the injector. The fluid path of the injector may optionally include a cannula 448 leading from cartridge 420 to a tube 449 to the injection needle of insertion assembly 433 and/or out into the patient. Optionally tube 449 is flexible and/or allows cannula 448 to move relative device 422 and/or insertion assembly 433 (for example cannula 448 may move along with bay 423 when bay 423 is opened and/or closed). Optionally cannula 448 is bent for example ranging between 90 to 85 degrees and/or between 85 to 60 degrees and/or between 60 to 45 degrees.

Insertion Assembly with a Hinged Cartridge Bay

Figure 5A:
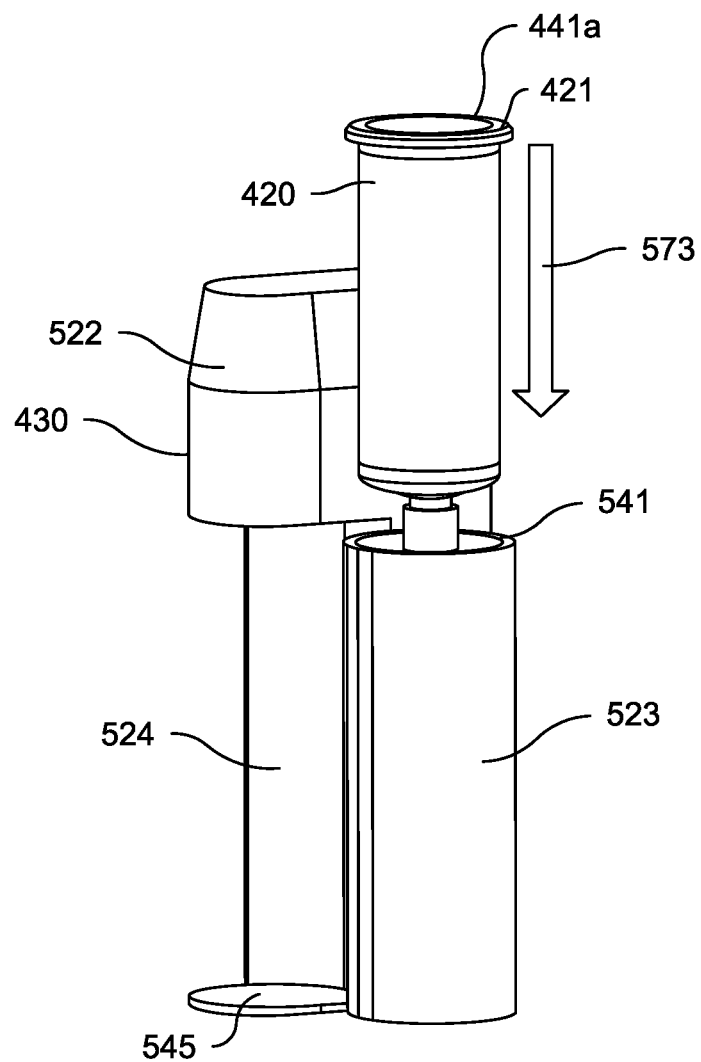
FIG. 5A is a perspective view of inserting a cartridge into a hinged bay in accordance with an embodiment of the present invention.

FIG. 5A is a perspective view of inserting a cartridge into a hinged bay in accordance with an embodiment of the present invention. In exemplary device 522, a cartridge bay 523 swings out to a loading position (for example as illustrated in FIG. 5A).

In the loading position, cartridge 420 may be inserted 573 through a proximal opening 541 into bay 523. For example the opening 541 may lead to a channel.

Optionally the channel is cylindrical and/or snugly fits the cartridge. A closed distal wall 545 optionally supports the distal end of bay 523. Optionally, bay 523 rotates to a closed position (for example as illustrated in FIG. 5C) wherein bay 523 and/or cartridge 520 inserted therein is coaxial with a cartridge compartment 524 and/or a cartridge pushing assembly.

Figure 5B:
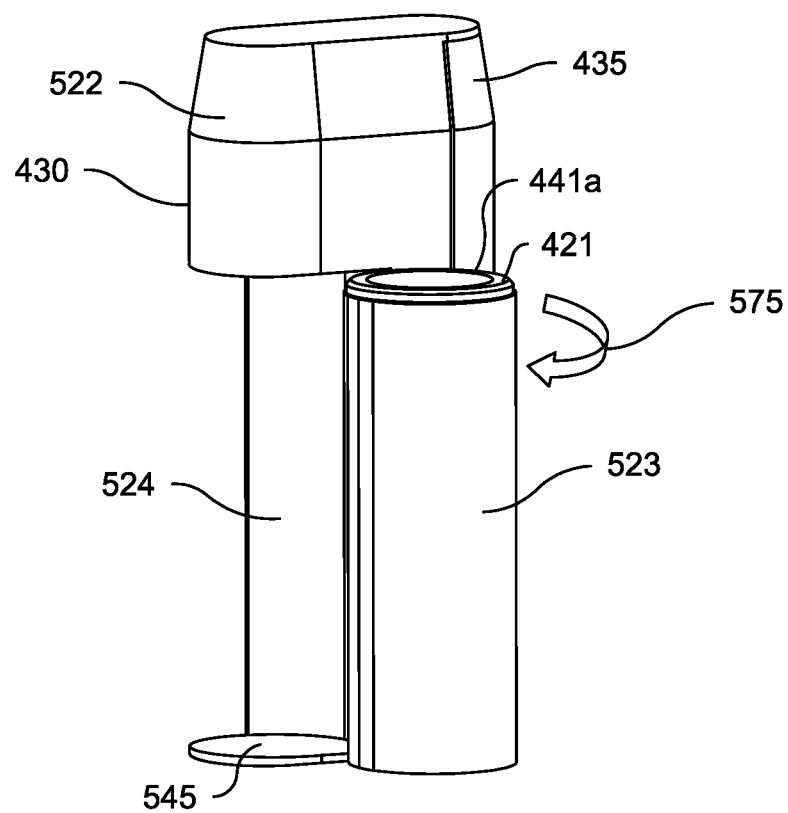
FIG. 5B is a perspective view of closing a hinged bay in accordance with an embodiment of the present invention.

FIG. 5B is a perspective view of a hinged bay in a loading position and loaded with a cartridge in accordance with an embodiment of the present invention. For example, once loaded, bay 523 is closed 575 into a distribution position by swinging around a movable, multiposition mount (for example a hinge 525 for example as illustrated in FIG. 5C).

Figure 5C:
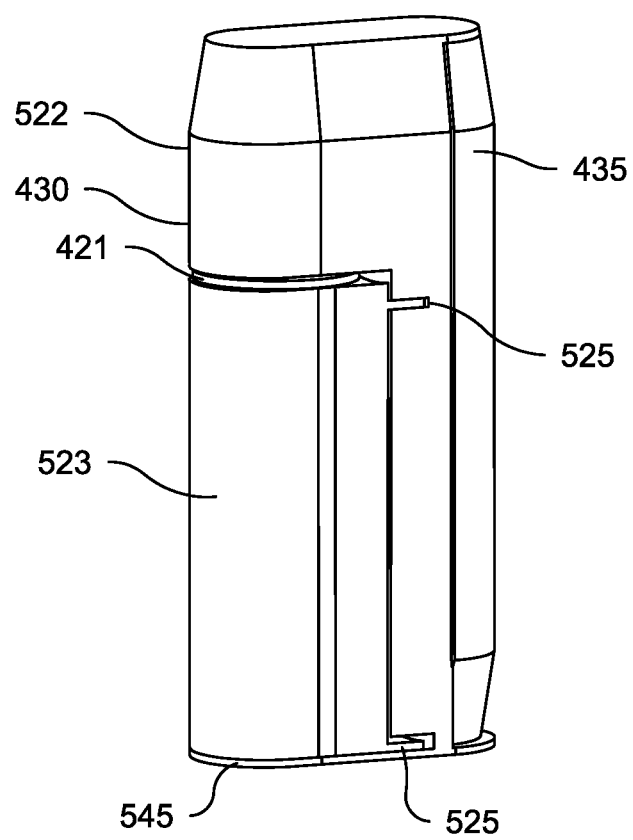
FIG. 5C is a perspective view of a closed hinged bay in accordance with an embodiment of the present invention.

FIG. 5C is a perspective view of a hinged bay in a distribution position in accordance with an embodiment of the present invention. The proximal end of device 422 optionally includes a stopper driving assembly as illustrated for example in FIG. 4D. Bay 523 optionally includes a cannula.

Figure 6A:
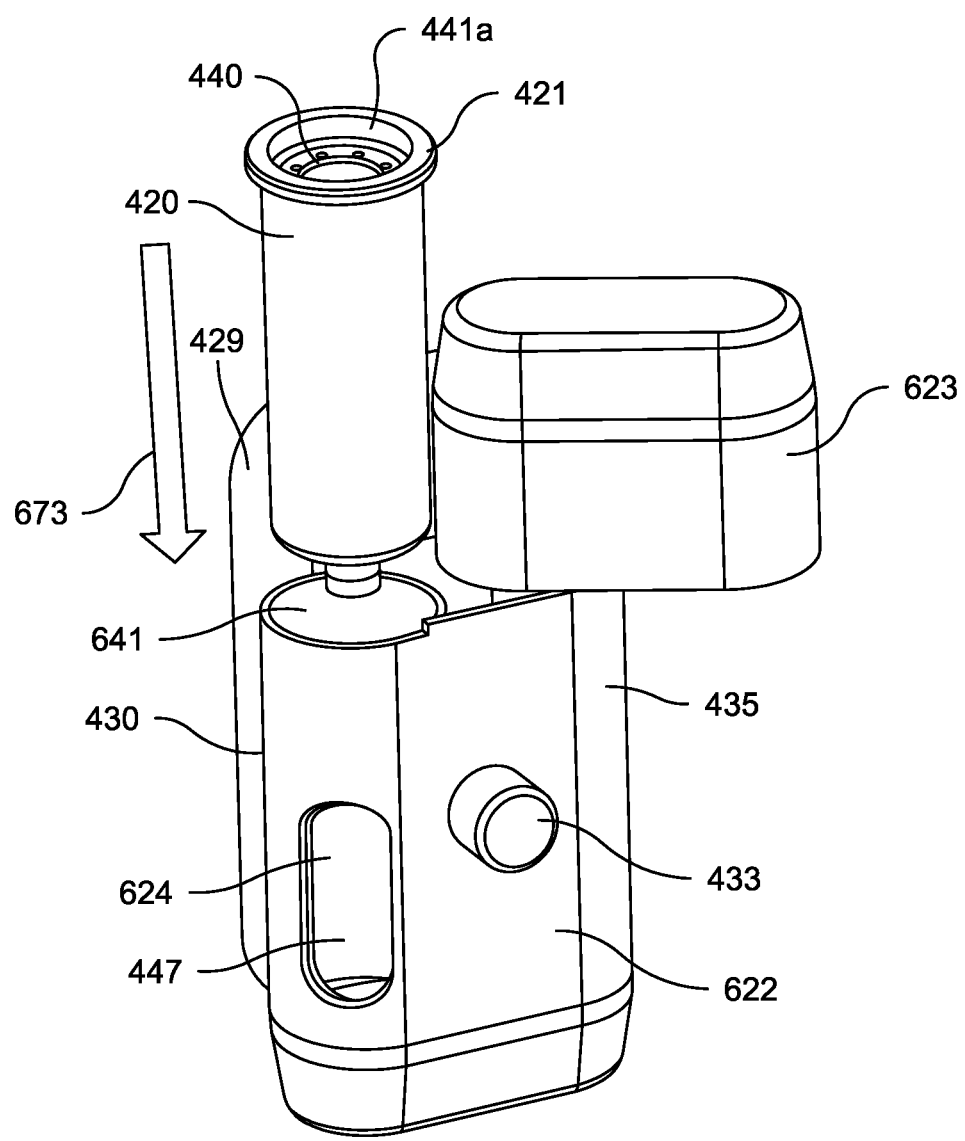
FIG. 6A is a perspective view of inserting a cartridge into a drug delivery device in accordance with an embodiment of the present invention.
Figure 6B:
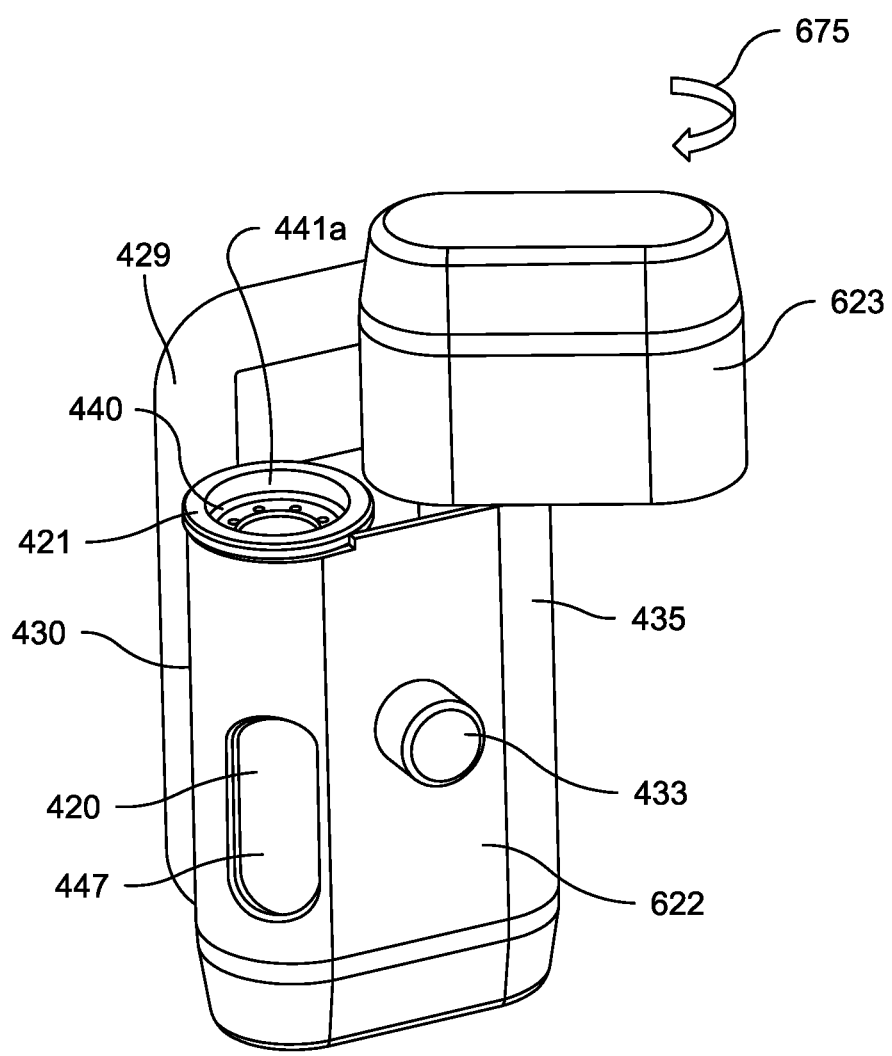
FIG. 6B is a perspective view of closing a hinged cover in accordance with an embodiment of the present invention.

FIG. 6A is a perspective view of inserting a cartridge into a drug delivery device in accordance with an embodiment of the present invention. For example, the device may have a hinged cover 623. For example the embodiment of FIGS. 6A-C does not include a cartridge bay. Optionally, in the loading position the proximal cover 623 of a device 622 swings open revealing an opening 641 to a cartridge compartment 624 (seen for example through window 447). Cartridge 420 may optionally be inserted 673 longitudinally into cartridge compartment 624. A cannula optionally protruding in the distal end of the cartridge compartment optionally pierces a septum on the distal end of cartridge 420 upon insertion 673 and/or connects cartridge 420 to a fluid path of device 622 upon insertion. Alternatively or additionally, the septum may be pierced after insertion. For example, the cartridge may be pushed into the coupler by the expanding assembly. FIG. 6B is a perspective view of a hinged cover device in a loading position after insertion of a cartridge in accordance with an embodiment of the present invention. After insertion 673 of cartridge 420, the proximal cover of device 623 optionally swings 675 closed.

Figure 6C:
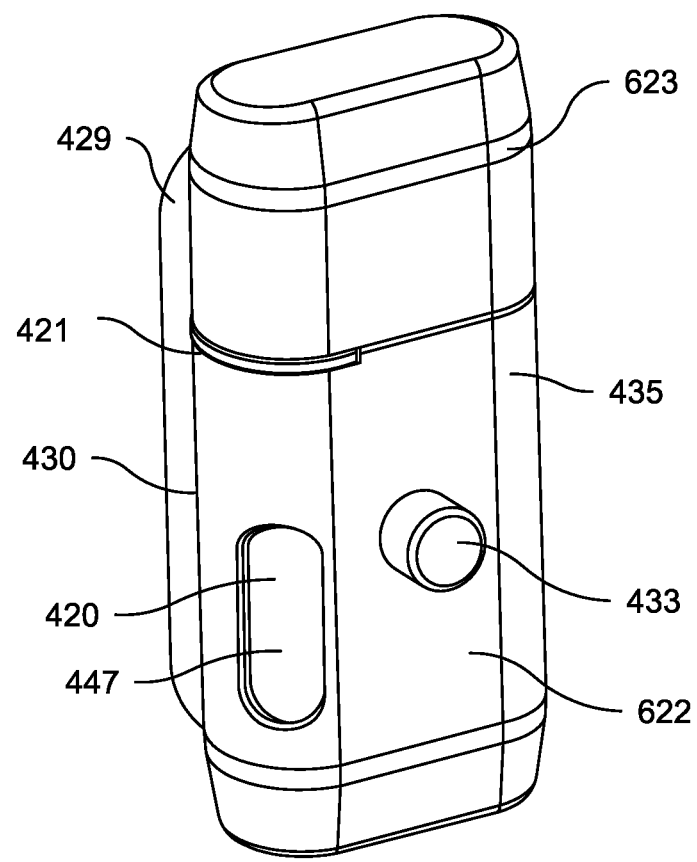
FIG. 6C is a perspective view of a closed hinged cover in accordance with an embodiment of the present invention.

FIG. 6C is a perspective view of a closed a hinged cover 623 in accordance with an embodiment of the present invention. Optionally a plunger pushing assembly is located in the proximal cover 623 and/or is positioned proximal to cartridge 420 when the cover is closed.

Figure 7A:
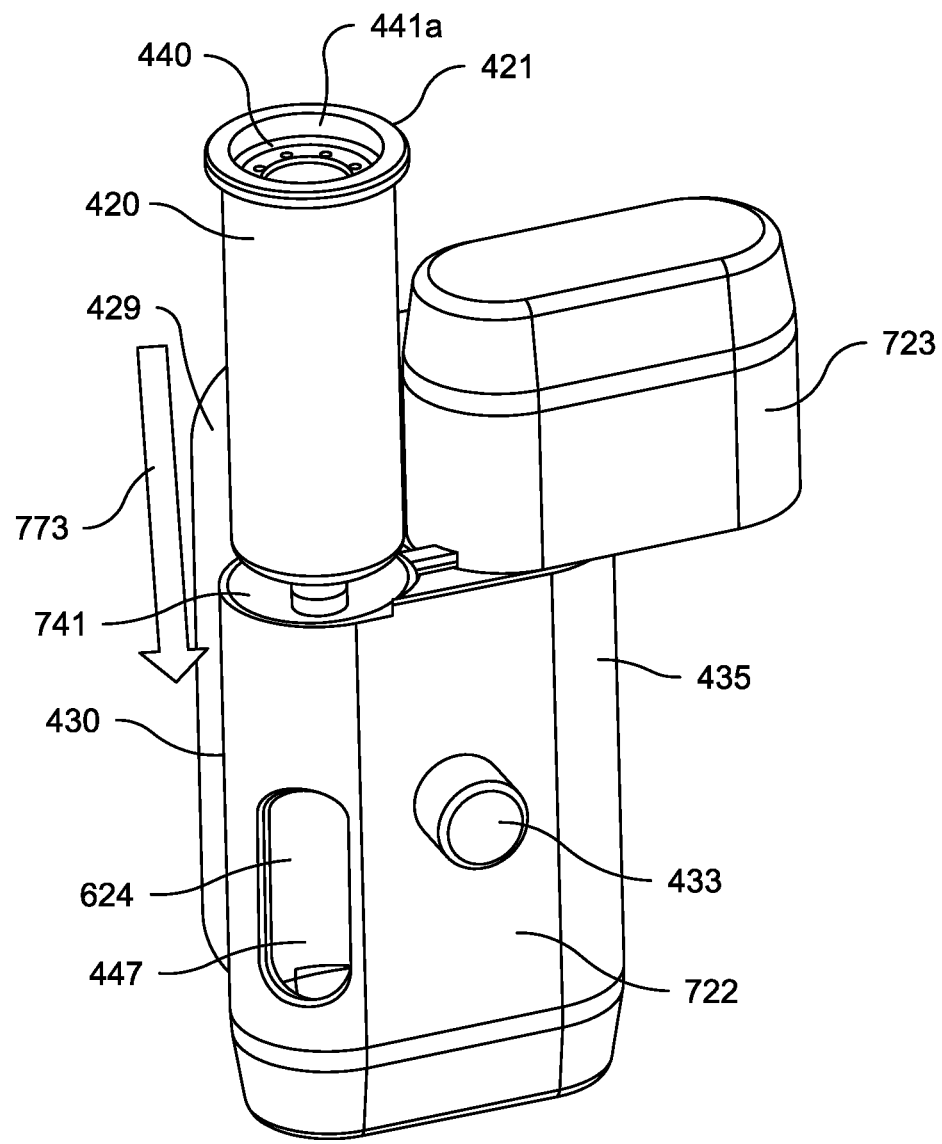
FIG. 7A is a perspective view of inserting a cartridge into a drug delivery device in accordance with an embodiment of the present invention.

FIG. 7A is a perspective view of inserting a cartridge into a drug delivery device in accordance with an embodiment of the present invention. For example device of FIGS. 7A-7C include a sliding cover 723. For example the embodiment of FIGS. 7A-7C do not include a cartridge bay. Optionally, in the loading position the proximal cover 723 of a device 722 slides open revealing an opening 741 to a cartridge compartment (seen for example through window 447). Cartridge 420 may optionally be inserted 773 longitudinally into cartridge compartment 724. A cannula optionally protrudes into the distal end of cartridge compartment 724. The cannula optionally pierces a septum on the distal end of cartridge 420 upon insertion 773 and/or connects cartridge 420 to a fluid path of device 722 upon insertion and/or after insertion.

Figure 7B:
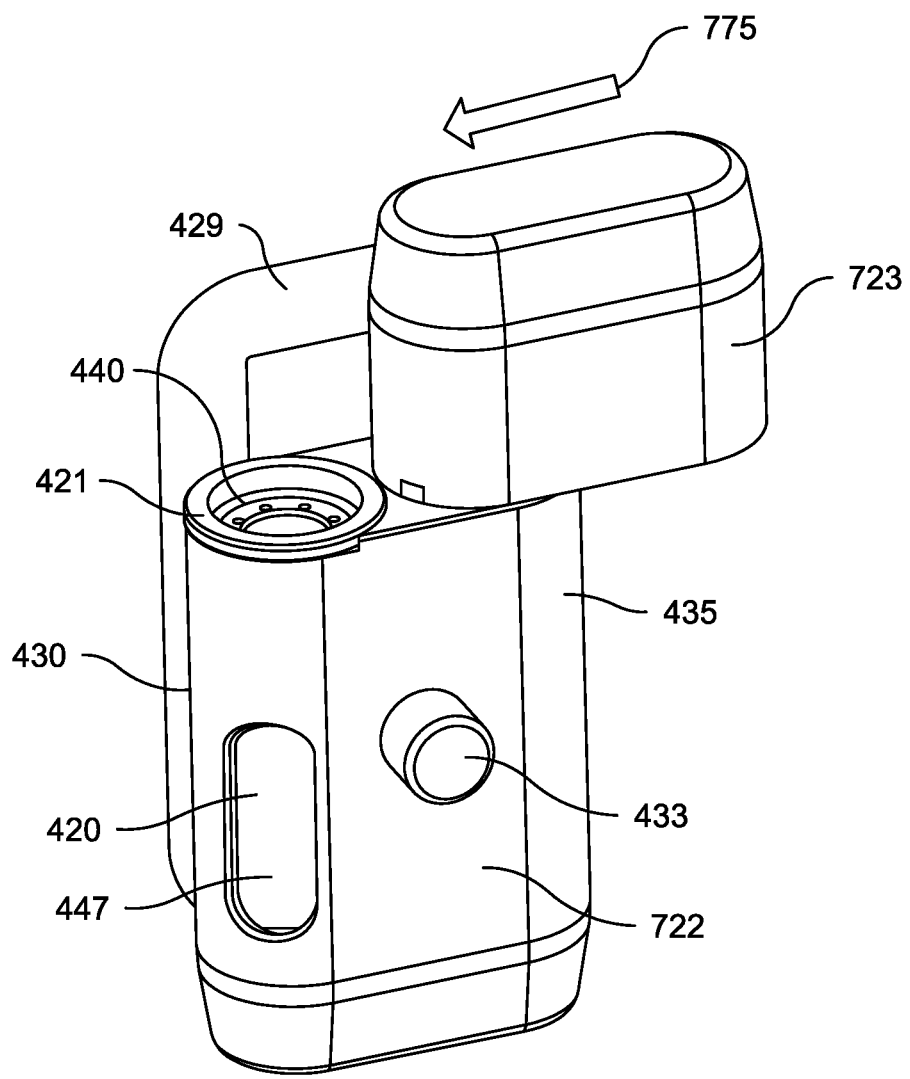
FIG. 7B is a perspective view of closing a sliding cover in accordance with an embodiment of the present invention.

FIG. 7B is a perspective view of a sliding cover device in a loading position after insertion of a cartridge in accordance with an embodiment of the present invention. After insertion 773 of cartridge 420, the proximal cover 723 of device 722 optionally slides 775 closed.

Figure 7C:
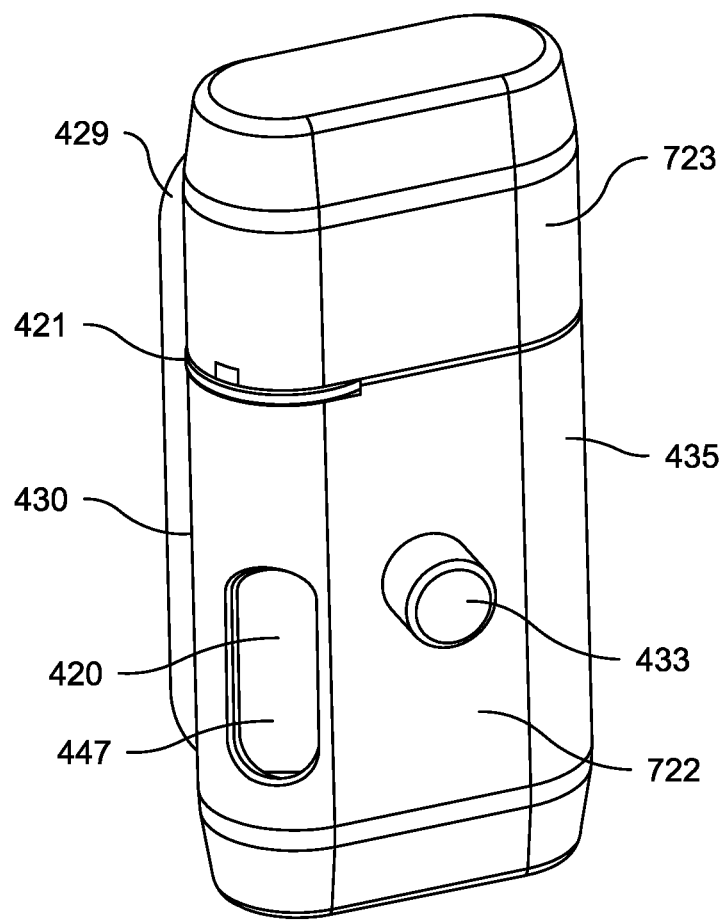
FIG. 7C is a perspective view of a closed sliding cover in accordance with an embodiment of the present invention.

FIG. 7C is a perspective view of a closed sliding cover 723 in accordance with an embodiment of the present invention. Optionally a plunger pushing assembly is located in the proximal cover 723 and/or is positioned proximal to cartridge 420 when cover 723 is closed.

A Stopper Driver with Anti-Rotational Guide Stabilized by the Device Housing

Figure 8A:
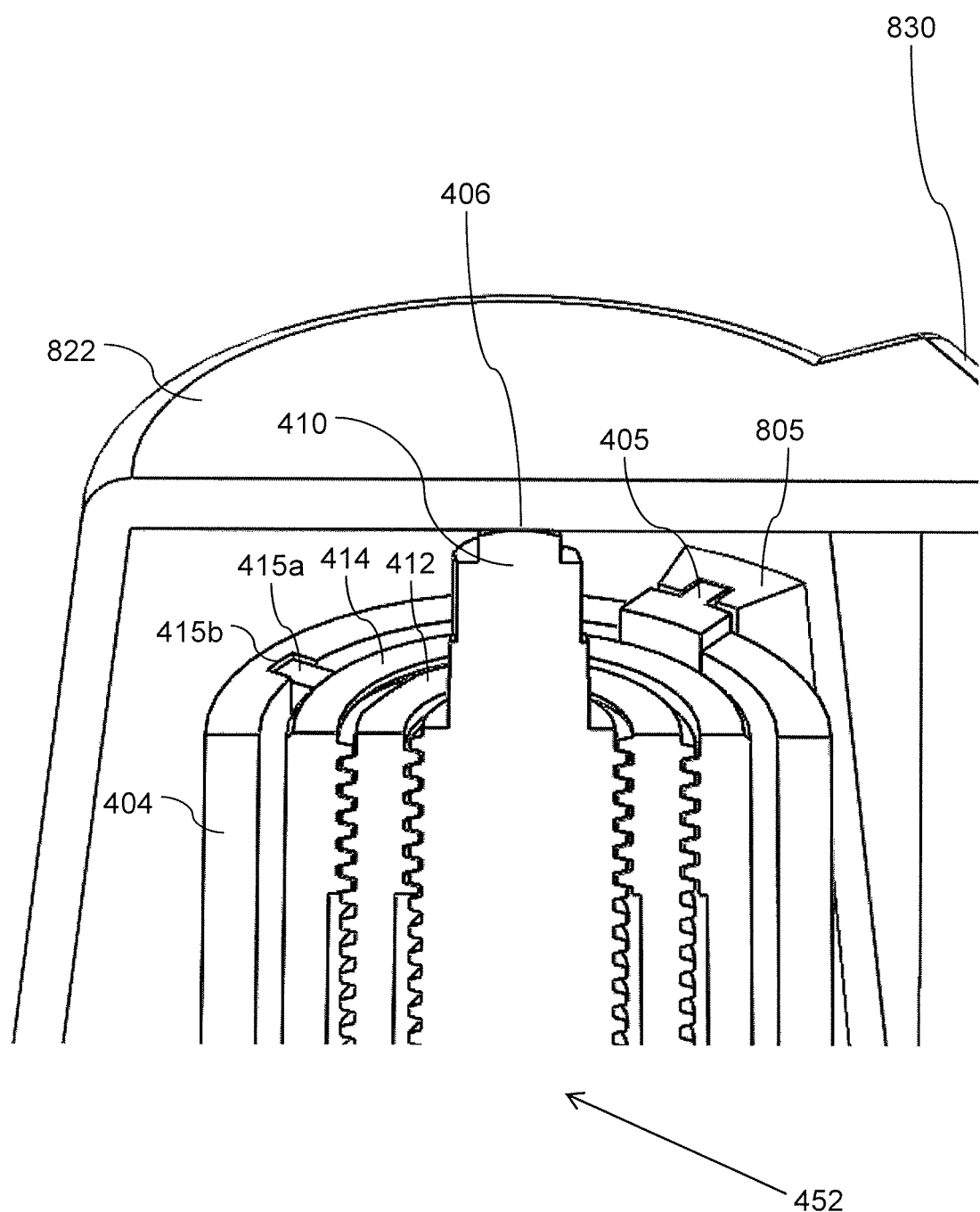
FIG. 8A is a close up cross sectional view of a stabilized stopper driver in a retracted configuration in accordance with an embodiment of the present invention.

FIG. 8A is a close up cross sectional view of a stopper driver in a contracted configuration in accordance with an embodiment of the present invention. In some embodiments, a TSA 452 is stabilized by a housing of a drug delivery device 822. For example, projection 405 of anti-rotational guide 404 connects to a guide track 805 that is attached to and/or intrinsic to the housing of device 822. Stopper driver shaft 410 is optionally linearly stabilized against the housing of device 822. For example, linear stabilization may be via a bearing 806. For simplicity the transmission and motor assembly are not shown in the FIGS. 8A-8B. Optionally device 822 has a skin contact surface 830.

Figure 8B:
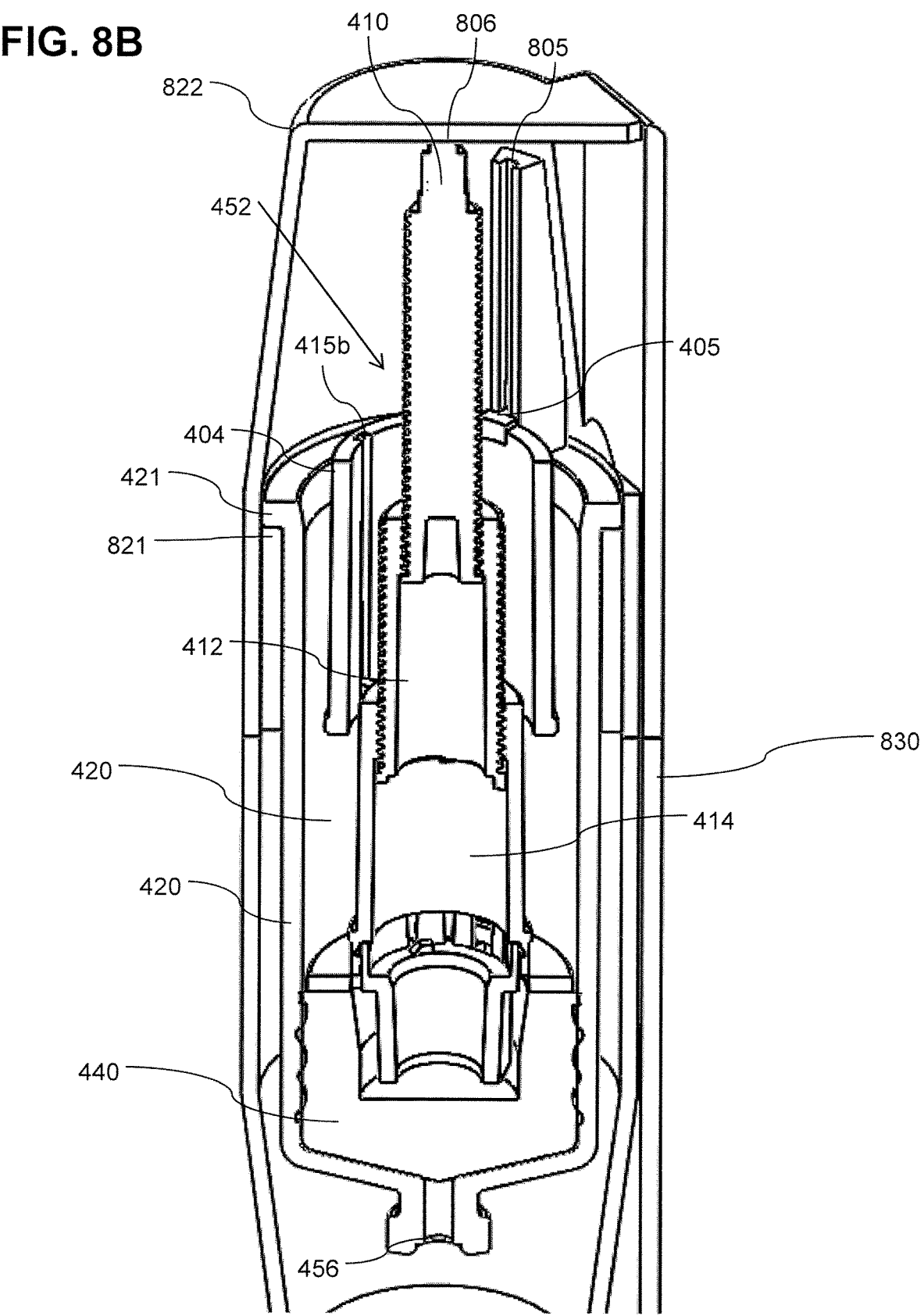
FIG. 8B is a cross sectional view of a reservoir and a stabilized stopper driver in an extended configuration in accordance with an embodiment of the present invention.

FIG. 8B is a cross-sectional view of a cartridge and a stopper driver in an extended configuration in accordance with an embodiment of the present invention.

Optionally stopper driver shaft 410 is rotated expanding TSA 452. For example TSA 452 expands into cartridge 420 and/or pushes plunger seal 440 into cartridge 420 and/or discharges a drug from cartridge 420. Optionally as TSA 452 expands, an anti-rotational guide moves into cartridge 420. For example projection 405 may slide down track 805 as anti-rotation guide 404 slides into cartridge 420 and/or projection 415a may slide down track 415b as stopper pushing shaft 414 slides with respect to anti rotation guide 404. A ridge 821 holds cartridge 420 from moving linearly distally with respect to device 822. Optionally contact surface 830 is parallel to an axis of a reservoir of cartridge 420 when cartridge 420 is inserted into a cartridge compartment of device 822 (for example in a delivery position). Optionally contact surface 830 is parallel to an axis of TSA 452. Optionally, and axis of expansion of TSA 452 is coaxial to cartridge 420 when cartridge 420 is inserted into a cartridge compartment of device 822.

Driving a Stopper

FIG. 9 is a flow chart illustrating a method of driving a plunger seal in accordance with an embodiment of the present invention. In some embodiments, a TSA may be extended or retracted by more than 100% its minimum length by rotating 910 a single shaft and/or by inhibiting rotation of a single shaft. For example, a TSA may be opened by rotating 910 a drive shaft. Optionally a proximal drive shaft may be located proximally to a distal pushing shaft. For example, the drive shaft may be rotated 910 with respect to a drug delivery device by a motor mounted on the device.

For example rotation 910 of the drive shaft may be with respect to the housing of the drug delivery device and/or with respect to a mount of the motor. Optionally, while the drive shaft is rotating, a pushing shaft may be inhibited 902 from rotating.

For example, an anti-rotational guide may prevent the pushing shaft from rotating with respect to the drug delivery device housing and/or with respect to the motor and/or with respect to a motor mount. Rotating 910 the drive shaft with respect to the pushing shaft optionally extends the TSA and/or the pushing shaft and/or a stopper.

In some embodiments and/or in some configurations, the mid shaft may axially move independently of the length of the TSA. For example, as the TSA is extended the mid shaft may either extend linearly 912 with the pushing shaft and/or rotate 913 with the drive shaft.

Optionally, for some lengths of the TSA, the position of the mid shaft may be indeterminate. For example, rotating 910 the drive shaft may, for example, extend 912 a mid-shaft into a reservoir (for example when the drive shaft rotates faster than the mid-shaft and/or by means of threading coupling the drive shaft to the mid shaft).

Optionally, extending 912 the mid-shaft into the reservoir simultaneously extends 914 the pushing shaft into the reservoir. Alternatively or additionally, rotating 910 the drive shaft may rotate 913 the mid-shaft. Optionally, rotating 913 the mid-shaft extends 914 a pushing shaft into the reservoir (for example by means of threading coupling the drive shaft to the mid shaft). Rotation and/or extension of the mid shaft may occur concurrently and/or sequentially.

In some embodiments, the anti-rotational guide may axially float. For example, when the TSA is extended the anti-rotational guide may either extend 904 (for example moving axially with respect to and/or into the reservoir) along with the pushing shaft and/or the anti-rotational guide may remain stationary with respect to the reservoir and/or the pushing shaft may extend 914 axially with respect to the anti-rotational guide. Optionally, for some lengths of the TSA, the position of the anti-rotational guide may be indeterminate.

Exemplary Dimensions of a Drug Delivery Device

In some embodiments the payload of a reservoir (for example a syringe) may include, for example between 0.5 and 3 ml and/or between 3 and 6 ml and/or between 6 and 10 ml and/or between 10 and 15 ml of a drug and/or more. Optionally the length of the reservoir (for example the length of the cylindrical portion of the cavity holding the drug) may range between 2 to 5 cm and/or between 5 to 10 cm.

Optionally the width of the reservoir (for example the inner width and/or diameter of the cylindrical portion of the cavity holding the drug) may range for example between 0.5 cm to 2 cm and/or between 2 to 5 cm. In some embodiments, the injector may discharge the entire payload as a single dose. A drug delivery device may include, for example, a pen injector and/or a patch injector, and/or an internally powered driver to drive the stopper and/or discharge the payload. The reservoir of the injector may be oriented parallel to the skin of a subject and/or perpendicular to the skin and/or at an angle between parallel and perpendicular, for example between 60 to 90 degrees and/or between 30 to 60 degrees and/or between 0 to 30 degrees.

For the sake of this application an internally powered injector driver may be defined as a drive mechanism powered by energy stored at least temporarily within the injector.

Power may be stored in a power supply, for instance as chemical potential (for example a chemical that produces an expanding gas and/or a battery) and/or mechanical potential (for example stored in an elastic member and/or a spring and/or a pressurized gas). For example the driver may be designed to discharge the payload over a time period ranging between 20 and 120 seconds and/or between 120 and 600 seconds and/or between 600 and 7200 seconds and/or longer. In some embodiments, discharge may be driven by a driver. An internally powered driver may be powered by various mechanisms including for example a motor (including for example a DC motor, an actuator, a brushless motor) and/or a transmission including for example a telescoping assembly and/or a threaded element and/or a gear and/or a coupling and/or an elastic mechanism (for example a spring and/or a rubber band) and/or an expanding gas and/or a hydraulic actuator).

A drug delivery device in accordance with some embodiments of the current invention may include reservoir. For example a reservoir may include a medicine container and/or a standard type syringe. Optionally a standard type syringe may be preloaded with medicine using standard equipment and/or in an aseptic room. A preloaded standard type syringe may optionally include a proximal opening. A stopper may optionally seal the proximal opening and/or protect the sterility of the contents of the syringe.

A sterile needle (for example a hollow needle) may optionally be connected to the syringe barrel. For example, the hollow of the needle may be in fluid communication with the interior of the barrel. The needle may optionally be rigidly attached to the distal end of the barrel. The sterility of all and/or part of the needle may for example be protected by a sterile cover. The sterile cover may remain on the needle when the syringe is supplied and/or installed into an injector. For example, the medicine container may optionally include a cylindrical barrel rigidly attached to a needle. Optionally, the long axes of the needle and barrel of the syringe may be parallel and/or coaxial. Optionally, the needle may be mounted on the distal end of the barrel. Optionally the needle point may be pointing in the distal direction. In some embodiments a stopper may slide axially along the inside of the barrel to discharge a medicine payload. For example, the medicine may be discharged through the hollow needle.

In some embodiments, the exposed length of the needle (for example protruding from the skin contact surface during drug discharge and/or during insertion of a cannula) may be suitable for performing an injection. For example, the exposed length of the needle may be suitable for intradermal injection and/or have gauge ranging for example between 24G to 30G and/or length ranging for example from 7-10 mm and/or the exposed length of the needle may be suitable for subcutaneous injection and/or have gauge ranging for example between 23G to 28G and/or length ranging for example from 9-28 mm and/or the exposed length of the needle may be suitable for intramuscular injection and/or have gauge ranging for example between 18G to 23G and/or length ranging for example from 24-40 mm and/or the exposed length of the needle may be suitable for intravenous injection and/or have gauge ranging for example between 15G to 22G and/or length ranging for example from 24-40 mm.

In some embodiments, a TSA may produce a force ranging for example between 0.02 to 0.2 N and/or between 0.2 and 0.5 N and/or between 0.5 to 5 N and/or between 5 to 60 N and/or between 60 to 90 N. For example the force required to inject the drug may depend on the injection rate and/or the viscosity of the drug and/or the syringe geometry and/or the needle dimensions.

In some embodiments, the stress to inject a medicine may include a torque.

For example, injection of medicine may be driven by a stopper. The stopper may optionally be driven by a threaded assembly, for example a threaded screw and/or teeth and/or a telescoping assembly. Optionally the pitch of the teeth and/or an associated screw may range for example between 0.5 to 2 mm and/or between 2 to 4 mm and/or between 4 to 8 mm. The diameter of the screw may range for example between 4 to 15 mm. The torque to power injection may range for example between 0.2 to 1.0 N*cm and/or between 1.0 to 10 N*cm.

During injection, the linear movement of a stopper may range for example between 5-40 mm and/or between 40-50 mm. The length of movement of the stopper may vary for example with the volume of medicine to be injected that may range for example between 0.5 to 3 ml and/or between 3 to 10 ml and/or between 10 to 30 ml.

It is expected that during the life of a patent maturing from this application many relevant technologies will be developed and the scope of the terms is intended to include all such new technologies a priori.

As used herein the term "about" refers to ±5%.

The terms "comprises", "comprising", "includes", "including", "having" and their conjugates mean "including but not limited to".

The term "consisting of" means "including and limited to".

The term "consisting essentially of" means that the composition, method or structure may include additional ingredients, steps and/or parts, but only if the additional ingredients, steps and/or parts do not materially alter the basic and novel characteristics of the claimed composition, method or structure.

As used herein, the singular form "a", "an" and "the" include plural references unless the context clearly dictates otherwise. For example, the term "a compound" or "at least one compound" may include a plurality of compounds, including mixtures thereof.

Throughout this application, various embodiments of this invention may be presented in a range format. It should be understood that the description in range format is merely for convenience and brevity and should not be construed as an inflexible limitation on the scope of the invention. Accordingly, the description of a range should be considered to have specifically disclosed all the possible subranges as well as individual numerical values within that range. For example, description of a range such as from 1 to 6 should be considered to have specifically disclosed subranges such as from 1 to 3, from 1 to 4, from 1 to 5, from 2 to 4, from 2 to 6, from 3 to 6 etc., as well as individual numbers within that range, for example, 1, 2, 3, 4, 5, and 6. This applies regardless of the breadth of the range. Whenever a numerical range is indicated herein, it is meant to include any cited numeral (fractional or integral) within the indicated range. The phrases "ranging/ranges between" a first indicate number and a second indicate number and "ranging/ranges from" a first indicate number "to" a second indicate number are used herein interchangeably and are meant to include the first and second indicated numbers and all the fractional and integral numerals therebetween.

It is appreciated that certain features of the invention, which are, for clarity, described in the context of separate embodiments, may also be provided in combination in a single embodiment. Conversely, various features of the invention, which are, for brevity, described in the context of a single embodiment, may also be provided separately or in any suitable subcombination or as suitable in any other described embodiment of the invention. Certain features described in the context of various embodiments are not to be considered essential features of those embodiments, unless the embodiment is inoperative without those elements.

All publications, patents and patent applications mentioned in this specification are herein incorporated in their entirety by reference into the specification, to the same extent as if each individual publication, patent or patent application was specifically and individually indicated to be incorporated herein by reference. In addition, citation or identification of any reference in this application shall not be construed as an admission that such reference is available as prior art to the present invention. To the extent that section headings are used, they should not be construed as necessarily limiting.

What is claimed is:

1. A drug delivery device having a skin contact surface, the drug delivery device comprising:
   a compartment defining a channel extending in a direction parallel to the skin contact surface and sized and shaped to receive a cartridge containing a drug, the channel defining a proximal opening sized and shaped for axial insertion of the cartridge;
   a coupler mounted to the drug delivery device at a distal end of the compartment to form a flow path between a distal opening of the cartridge and a fluid path of the drug delivery device;
   a cover hingedly attached to the drug delivery device, the cover being movable between a closed position, blocking the cartridge from insertion into the proximal opening of the channel, and a loading position, clearing the proximal opening of the channel for cartridge insertion, and
   a plunger pushing assembly housed within the cover and movable therewith, the cover positioning the plunger pushing assembly proximal to the channel to face the proximal opening thereof in the closed position of the cover, the plunger pushing assembly being expandable along an axis parallel to the compartment and the skin contact surface.

2. The device of claim 1, wherein the coupler includes a cannula for piercing a septum at the distal opening of the cartridge, and the fluid path connects the cannula with an injection needle of the drug delivery device.

3. The device of claim 2, wherein the cannula pierces the septum upon insertion of the cartridge into the channel.

4. The device of claim 2, wherein the cannula pierces the septum after insertion of the cartridge into the channel and upon expansion of the plunger pushing assembly, pushing the cartridge into the coupler.

5. The device of claim 1, wherein the coupler protrudes axially into the distal end of the compartment.

6. The device of claim 1, wherein the plunger pushing assembly comprises a telescoping screw.

7. The device of claim 1, wherein an injection needle extends outwardly from the skin contact surface.

8. The device of claim 1, wherein the cartridge has a flange.

9. The device of claim 1, wherein the cover is rotatable about an axis parallel to the axis along which the plunger expands.

10. The device of claim 1, wherein when the cartridge is disposed within the channel, the plunger pushing assembly is configured to transition from a first position, where the plunger pushing assembly is spaced in an entirety from a stopper disposed within the cartridge, to a second position, where the plunger pushing assembly engages the stopper.

11. A method of loading a cartridge containing a drug into a drug delivery device having a skin contact surface, the drug delivery device comprising a compartment defining a channel extending in a direction parallel to the skin contact surface and sized and shaped to receive the cartridge, the channel defining a proximal opening sized and shaped for axial insertion of the cartridge, a coupler mounted to the drug delivery device at a distal end of the compartment to form a flow path between a distal opening of the cartridge and a fluid path of the drug delivery device, a cover hingedly attached to the drug delivery device and housing a plunger pushing assembly therein,
   the method comprising the steps of:
   swinging the cover from a closed position thereof, blocking the cartridge from insertion into the channel via the proximal opening, to a loading position thereof, clearing the proximal opening of the channel for cartridge insertion;
   inserting the cartridge into the channel; and
   swinging the cover, and the plunger pushing assembly within, from the loading position to the closed position, thereby positioning the plunger pushing assembly proximal to the channel and facing the proximal opening thereof,
   the plunger pushing assembly being expandable along an axis parallel to the compartment and the skin contact surface.

12. The method of claim 11, wherein the coupler includes a cannula for piercing a septum at the distal opening of the cartridge, and the inserting step comprises piercing the septum with the cannula, and, in turn, forming the flow path between the distal opening of the cartridge and the fluid path of the drug delivery device.

13. The method of claim 11, wherein the coupler includes a cannula for piercing a septum at the distal opening of the cartridge, and further comprising the steps of expanding the plunger pushing assembly through a proximal opening of the cartridge to engage the cartridge and piercing the septum with the cannula, and, in turn, forming the flow path between the distal opening of the cartridge and the fluid path of the drug delivery device.

14. The method of claim 11, wherein swinging the cover includes rotating the cover about an axis parallel to the axis along which the plunger expands.

15. The method of claim 11, wherein rotating the drive shaft includes transitioning the plunger pushing assembly from a first position, where the plunger pushing assembly is spaced in an entirety from a stopper disposed within the cartridge, to a second position, where the plunger pushing assembly engages the stopper.

* * * * *